(12) United States Patent
Bossé et al.

(10) Patent No.: US 8,859,291 B2
(45) Date of Patent: Oct. 14, 2014

(54) METHODS FOR TARGET MOLECULE DETECTION USING SIDEROPHORES AND RELATED COMPOSITIONS

(75) Inventors: Roger Bossé, Longueuil (CA); Wayne F. Patton, Newton, MA (US); Philippe Roby, Pointe-Claire (CA)

(73) Assignee: PerkinElmer LAS, Inc., Wellesley, MA (US)

( * ) Notice: Subject to any disclaimer, the term of this patent is extended or adjusted under 35 U.S.C. 154(b) by 12 days.

(21) Appl. No.: 11/148,478

(22) Filed: Jun. 9, 2005

(65) Prior Publication Data

US 2006/0019279 A1    Jan. 26, 2006

Related U.S. Application Data

(60) Provisional application No. 60/521,956, filed on Jul. 27, 2004, provisional application No. 60/521,644, filed on Jun. 9, 2004.

(51) Int. Cl.

| | | |
|---|---|---|
| *G01N 33/00* | (2006.01) | |
| *G01N 25/18* | (2006.01) | |
| *G01N 27/00* | (2006.01) | |
| *G01N 21/62* | (2006.01) | |
| *G01N 21/76* | (2006.01) | |
| *G01N 24/00* | (2006.01) | |

(52) U.S. Cl.
USPC ........... 436/103; 436/104; 436/105; 436/106; 436/119; 436/120; 436/123; 436/114; 436/115; 436/107; 436/149; 436/171; 436/172; 436/173

(58) Field of Classification Search
None
See application file for complete search history.

(56) References Cited

U.S. PATENT DOCUMENTS

| | | | | |
|---|---|---|---|---|
| 5,154,903 | A | * | 10/1992 | Graceffa et al. ............ 423/326 |
| 5,371,234 | A | * | 12/1994 | Hancock .................... 548/339.1 |
| 5,997,912 | A | | 12/1999 | Schlesinger et al. |
| 6,180,354 | B1 | | 1/2001 | Singh et al. |
| 6,203,822 | B1 | | 3/2001 | Schlesinger et al. |
| 6,251,581 | B1 | | 6/2001 | Ullman et al. |
| 7,102,005 | B2 | * | 9/2006 | Agnew et al. ................ 544/287 |
| 2004/0038306 | A1 | | 2/2004 | Agnew et al. |
| 2004/0146950 | A1 | * | 7/2004 | Howe ............................. 435/7.2 |
| 2004/0171034 | A1 | * | 9/2004 | Agnew et al. .................... 435/6 |
| 2006/0063219 | A1 | | 3/2006 | Kuo et al. |

FOREIGN PATENT DOCUMENTS

| | | | |
|---|---|---|---|
| WO | WO 93/17714 | * | 9/1993 |
| WO | WO-2004042347 | | 5/2004 |

OTHER PUBLICATIONS

Schwyn et al. Analytical Biochemistry 160 (1987): 47-56.*
Ramadan et al. Journal of Chromatography, 321 (1985) 93-104.*
deMan et al. Principles of Food Chemistry, 3rd Edition 1999, p. 151.*
Renshaw et al. Mycological Research 106 (2002): 1123-1142.*
Guo et al. The Journal of Biological Chemistry. Jan. 2003 vol. 278 p. 2490-2502.*
Terefe et al Biotechnol. Prog. 2002, 18, 1249-1256.*
Slomczynska et al (in Peptides: The Wave of the Future. Michel Lebl and Richard Houghten (Editors) American Peptide Society, 2001).*
Elo et al Biochem J. Apr. 1974; 140(1): 115-116.*
Marshall et al. Advances in Supramolecular chemistry. vol. 8, Gokel, Gw., Ed., Cerberus Press, Inc, 2002, pp. 174-243.*
Yokoyama et al. J Nucl. Med 23:909-914, 1982.*
Moorman et al. Molecular and Biochemical Parasitology 98 (1999)279-283.*
Organic Chemistry, 6th Edition, p. 164, William H. Brown et al, Christopher S. Foote, Brent L. Iverson, Eric V Anslyn, Bruce M Novak, 2011.*
Al-Aoukaty et al., Gallium toxicity and adaptation in *Pseudomonas fluorescens*, FEMS Microbiol. Lett., 1992, vol. 71(3), pp. 265-272.
Arceneaux et al., Enhancement of copper toxicity by siderophores in *Bacillus megaterium*, Antimicrob. Agents Chemother., 1984, vol. 25(5), pp. 650-652.
Atkinson et al., Bacterial iron transport: 1H NMR determination of the three-dimensional structure of the gallium complex of pyoverdin G4R, the peptidic siderophore of *Pseudomonas putida* G4R, Biochemistry, 1998, vol. 37(45). pp. 15965-15973.
Brill et al., Robust phosphoproteomic profiling of tyrosine phosphorylation sites from human T cells using immobilized metal affinity chromatography and tandem mass spectrometry, Anal. Chem., 2004, vol. 76(10), pp. 2763-2772.
Buhl et al., Application of chrome azurol S and benzyldodecyldimethylammonium bromide for gallium determination in mineral fertilizers, Chem. Anal. (Warsaw), 2002, vol. 47, p. 163-167.
Burton et al., Hydrophobic charge induction chromatography: salt independent protein adsorption and facile elution with aqueous buffers, J. Chromatogr. A, 1998, vol. 814, pp. 71-81.
Chelators for Iron Overload as retrieved on Oct. 24, 2006 from http://sickle.bwh.harvard.edu/chelators.html.
Clarke et al., Induction of siderophore activity in *Anabaena* spp. and its moderation of copper toxicity, Appl. Environ. Microbiol., 1987, vol. 53(5), pp. 917-922.
Cutting et al., Staining of phospho-proteins on acrylamide gel electropherograms, Anal. Biochem., 1973, vol. 54(2), pp. 386-394.
Debruyne, Staining of alkali-labile phosphoproteins and alkaline phospatases on polyacrylamide gels, Anal. Biochem.. 1983, vol. 133(1), pp. 110-115.

(Continued)

*Primary Examiner* — Oluwatosin Ogunbiyi
(74) *Attorney, Agent, or Firm* — Wilmer Cutler Pickering Hale and Dorr LLP

(57) ABSTRACT

The invention provides methods for isolating a target molecule from a sample. In an embodiment, the method involves contacting a sample with a capture agent, the agent comprising a siderophore and a transition metal cation, under conditions wherein the agent is capable of binding a target molecule to form a target molecule-capture agent complex, wherein the target molecule is selected from the group consisting of a phosphorylated molecule, a nitrotyrosine-containing molecule and a sulfated molecule, and separating the target molecule-capture agent complex from the sample, thereby isolating the target molecule from the sample. Also provided are methods for determining the presence of a target molecule in a sample, that involve contacting a sample with a capture agent, the agent comprising a siderophore and a transition metal cation.

16 Claims, 5 Drawing Sheets

(56) References Cited

OTHER PUBLICATIONS

Dong et al., Total synthesis of exochelin MN and analogues, J. Org. Chem., 2002, vol. 67(14), pp. 4759-4770.

Ficarro et al., Phosphoproteome analysis by mass spectrometry and its application to *Saccharomyces cerevisiae*, Nat. Biotechnol., 2002, vol. 20(3), pp. 301-305.

Feistner et al., Proferrioxamine siderophores of *Erwinia amylovora*. A capillary liquid chromatopraphic/electrospray tandem mass spectrometirc study, Organic Mass Spectrometry, 2005, 28(3):163-175.

Folschweiller et al., The interaction between pyoverdin and its outer membrane receptor in *Pseudomonas aeruginosa* leads to different conformers: a time-resolved fluorescence study, Biochemistry, 2002, vol. 41(49), pp. 14591-14601.

Gabricevic et al., Kinetics and mechanism of iron(III)-nitrilotriacetate complex reactions with phosphate and acetohydroxamic acid, Inorg. Chem., 2003, vol. 42(13), pp. 4098-4101.

Gilis et al., Siderophore-mediated iron uptake in *Alcaligenes eutrophus* CH34 and identification of aleB encoding the ferric iron-alcaligin E receptor, J. Bacteriol., 1996, vol. 178(18), pp. 5499-5507.

Heggemann et al., Trishydroxamates and triscatcholates based on monosaccharides and myo-inositol as artificial siderophores, Biometals., 2003, vol. 16(4), pp. 539-551.

Hou et al., Preorganized siderophore: thermodynamic and structural chracterication of alcaligin and bisucaberin, microbial macrocyclic dihydroxamate chelating agents (1), Inorg. Chem., 1998, vol. 37(26), pp. 6630-6637.

Iijima et al., IC202A, a new siderophore with immunosuppressive activity produced by *Streptoalloteichus* sp. 1454-19. II. Physico-chemical properties and structure elucidation, J. Antibiot. (Tokyo), 1999, vol. 52(1), pp. 25-28.

Iijima et al., IC202A, a new siderophore with immunosuppressive activity produced by *Streptoalloteichus* sp. 1454-19. I. Taxonomy, fermentation, isolation and biological activity, J. Antibiot. (Tokyo), 1999, vol. 52(1), pp. 20-24.

Kaffashan et al., Evaluation of Commercially Available IMAC Kits: Millipore ZipTipMC, Eprogen IPAC beads and Pierce Swellgel Gallium Chelated Disks, retrieved on Oct. 24, 2006 from www.eprogen.com/proteomics/literature/ASMS_Poster_2003-Biogen.pdf.

Kilz et al., A fast screening method for the identification of siderophores from fluorescent *Pseudomonas* spp. by liquid chromatography/electrospray mass spectrometry, J. Mass Spectrom., 1999, vol. 34(4), pp. 281-290.

Martin et al., Strategies and solid-phase formats for the analysis of protein and peptide phosphorylation employing a novel fluorescent phosphorylation sensor dye, Comb. Chem. High Throughput Screen, 2003, vol. 6(4), pp. 331-339.

Martin et al., Quantitative analysis of protein phosphorylation status and protein kinase activity on microarrays using a novel fluorescent phosphorylation sensor dye, Proteomics, 2003, vol. 3(7), pp. 1244-1255.

McKnight et al., Release of weak and strong copper-complexing agents by algae, Liminol Oceanogr., 1979, vol. 24, pp. 823-837.

McKnight et al., Copper complexation by siderophores from filamentous blue-green algae, Liminol. Oceanogr., 1980, vol. 25, pp. 62-71.

Meyer, Pyoverdines: pigments, siderophores and potential taxonomic markers of fluorescent *Pseudomonas* species, Arch. Microbiol., 2000, vol. 174(3), pp. 135-142.

Moberg et al., Fingerprinting metal-containing biomolecules after reductive displacement of iron by gallium and subsequent column-switched LC-ICPMS analysis applied on siderophores, Anal. Chem., 2004, vol. 76(9). pp. 2618-2622.

Moss et al., Remarkable acceleration of dimethyl phosphate hydrolysis by ceric cations, Chem. Commun., 1998, pp. 1871-1872.

Napper et al., Selective extraction and characterization of a histidine-phosphorylated peptide using immobilized copper(II) ion affinity chromatography and matrix-assisted laser desorption/ionization time-of-flight mass spectrometry, Anal. Chem., 2003, vol. 75(7), pp. 1741-1747.

Neilands, Siderophores: structure and function of microbial iron transport compounds, J. Biol. Chem., 1995, vol. 270(45), pp. 26723-26726.

Olakanmi et al., Gallium disrupts iron metabolism of mycobacteria residing within human macrophages, Infect. Immun., 2000, vol. 68(10), pp. 5619-5627.

Palanche et al., Fluorescent siderophore-based chemosensors: iron(III) quantitative determinations, J. Biol. Inorg. Chem., 1999, vol. 4(2), pp. 188-198.

Payne, Detection, isolation, and characterization of siderophores, Methods Enzymol., 1994, vol. 235, pp. 329-344.

Persmark et al., Iron(III) complexes of chrysobactin, the siderophore of *Erwinia chrysanthemi*, Biometals, 1992, vol. 5(1), pp. 29-36.

Poreddy et al., Hydroxamate-based iron chelators: combinatorial syntheses of desferrioxamine B analogues and evaluation of binding affinities, J. Comb. Chem., 2004, vol. 6(2), pp. 239-254.

Posewitz et al., Immobilized gallium(III) affinity chromatography of phosphopeptides, Anal. Chem., 1999, vol. 71(14), pp. 2883-2892.

Schulenberg et al., Analysis of steady-state protein phosphorylation in mitochondria using a novel fluorescent phosphosensor dye, J. Biol. Chem., 2003, vol. 278(29), pp. 27251-27255.

Schwyn et al., Universal chemical assay for the detection and determination of siderophores, Anal. Biochem., 1987, vol. 160(1), pp. 47-55.

Shu et al., Identification of phosphoproteins and their phosphorylated sites in the WEHI-231 B lymphoma cell line, Molecular & Cellular Proteomics 3.3, 2004, pp. 279-286.

Slomczynska et al., Hydroxamate analog libraries and evaluation of their iron affinity, Transfus Sci., 2000, vol. 23(3), pp. 265-266.

Smith et al., Rhizobactin, a siderophore from *Rhizobium meliloti*, J. Plant Nutr., 1984, vol. 7, pp. 449-458.

Steinberg et al., Global quantitative phosphoprotein analysis using multiplexed proteomics technology, Proteomics, 2003, vol. 3(7), pp. 1128-1144.

Szarapinska-Kwaszewska et al., Synthesis of siderophores by strains of *Staphylococcus cohnii* isolated from various environments, Acta Microbiol. Pol., 2003, vol. 52(3), pp. 261-269.

Toth et al., Determination of aluminum(III) in crystallized fruit samples using a multicommutated flow system, J. Agric. Food Chem., 2004, vol. 52(9), pp. 2450-2454.

Ullman et al., Luminescent oxygen channeling immunoassay: measurement of particle binding kinetics by chemilunimescence, Proc. Natl. Acad. Sci. USA, 1994, vol. 91, pp. 5426-5430.

Wasielewski et al., The three-dimensional structure of the gallium complex of azoverdin, a siderophore of azomonas macrocytogenes ATCC 12334, determined by NMR using residual dipolar coupling constants, Biochemistry, 2002, vol. 41(41), pp. 12488-12497.

Yguerabide et al., Resonance light scattering particles as ultrasensitive labels for detection of analytes in a wide range of applications, J. Cell Biochem. Suppl., 2001, vol. Suppl. 37, pp. 71-81.

Zhao et al., Surface phosphophilicity of aluminum-containing adjuvants probed by their efficiency for catalyzing the P—O bond cleavage with chromogenic and fluorogenic substrates, Anal. Biochem, 2001, vol. 295(1), pp. 76-81.

Australian Examination Report issued for Application No. 2005254970, issued Nov. 30, 2009 (3 pages).

Supplementary European Search report mailed Mar. 3, 2010 for European Patent application No. 05762180.7 filed Jun. 9, 2005.

Zhou et al., "Detection and sequencing of phosphopeptides affinity bound to immobilized metal ion beads by matrix-assisted laser desorption/ionization mass spectrometry," Journal of the American society for mass spectrometry, vol. 11, pp. 273-282 (Apr. 1, 2000).

Slomczynska et al., "Combinatorial Sytheses of Polyhydroxamate Siderophores: Desferrioxamine, Exochelin, Mycobactin, and Aerobactin Libraries," Peptide: the wave of the Future, pp. 177-178 (2001).

"AlphaScreen PhosphoSensor," Perkin Elmer Brochure (2006) (4 pages).

(56) References Cited

OTHER PUBLICATIONS

Attwood et al., "Focus on phosphohistidine," Amino Acids, vol. 32, pp. 145-156 (2007).

Dill et al., "Denatured states of proteins," Annu. Rev. Biochem., vol. 60, pp. 795-825 (1991).

Duclos et al., "Chemical properties and separation of phosphoamino acids by thin-layer chromatography and/or electrophoresis," Methods in Enzymology, vol. 201, pp. 10-21 (1991).

Sankar et al., "Buffers for the Physiological pH Range: Thermodynamic Constants of 3-(N-Morpholino)propanesulfonic Acid from 5 to 50° C," Analytical Chemistry, vol. 50, pp. 1922-1924 (Nov. 1978).

De Man, Principles of Food Chemistry, Third Edition, pp. 151-152, 1999.

Millipore Technical Note "Enrichment of Phosphopeptides Before MALDI-TOF and Nanoelectrospray MS Using ZipTipmc Pipette Tips", Feb. 27, 2001.

Napper, et al., "Selective Extraction and Characterization of a Histidine-Phosphorylated Peptide Using Immobilized Copper (II) Ion Affinity Chromatography and Matrix-Assisted Laser Desorption/Ionization Time-of-Flight Mass Spectrometry", Anal. Chem., 75:1741-1747 (2003).

Ramadan, et al., "$Fe^{3+}$-Hydroxamate as Immobilized Metal Affinity Adsorbent for Protein Chromatography", Journal of Chromatography, 321:93-104 (1985).

Renshaw, et al., "Fungal Siderophores: Structures, Functions, and Applications", Mycol. Res., 106(10):1123-1142 (2002).

International Search Report and Written Opinion issued for PCT/US05/20152, dated Dec. 12, 2007.

\* cited by examiner

METHODS FOR TARGET MOLECULE DETECTION USING SIDEROPHORES AND RELATED COMPOSITIONS

This application claims the benefit of U.S. Provisional Application No. 60/521,956, filed Jul. 27, 2004, and U.S. Provisional Application No. 60/521,644, filed Jun. 9, 2004, which are incorporated herein by reference.

BACKGROUND

The present invention relates generally to detecting and isolating target molecules and, more specifically, to detecting and isolating phosphomolecules, nitrotyrosine-containing molecules and sulfated molecules.

Cells of the body contain many types of molecules that vary in function, size, lifetime, and numerous other characteristics. Some of these molecules are unchanged during their lifetime within the body, while other molecules become modified through chemical reactions. The modifications can be indicative of particular cell states, including normal states as well as abnormal states caused by injury, infection and disease.

In particular, many proteins are chemically modified during their lifetime in the body. Accordingly, a protein can include any number of modifications that occur during and after its synthesis within the cell. These modifications change the size and the structure of the protein, thereby often changing the protein's function or behavior in the cell. An example of a possible modification of a protein is enzymatic cleavage of the original polypeptide by proteases to produce a smaller product. Other modifications include the addition of sugar molecules to certain amino acids in the protein (glycosylation), the addition of a phosphate group (phosphorylation), the addition of a sulfate group (sulfation) and the addition of a nitro group on a tyrosine residue (tyrosine nitrosylation).

Reversible phosphorylation of threonine, serine, and tyrosine residues by enzymes called kinases (which add a phosphate) and phosphatases (which remove the phosphate) plays an important role in regulating many cell processes, such as growth and cell cycle control. Phosphorylation can occur sequentially from one protein to another, resulting in a series of activations called a "phosphorylation cascade." Phosphorylation cascades are recognized as signaling networks that direct growth, death, and differentiation of cells—the critical signals for maintaining normal cells in the body. Efforts are underway within the research community to identify phosphorylated proteins of various cell types, the population of phosphorylated proteins being referred to as the "phosphoproteome." Increased understanding of protein phosphorylation has already led to development of effective cancer therapies, such as Herceptin® and Erbitux®.

Nitrotyrosine has been shown to be present in proteins from a variety of clinical conditions including atherosclerotic lesions of human coronary arteries, postischemic heart, and placenta during preeclampsia, inflammatory disease, and neurological disease, such as amyotrophic lateral sclerosis (ALS). Researchers also have reported that nitrotyrosine levels were reduced among patients treated with statins, a commonly used class of cholesterol-lowering drugs, indicating that nitrotyrosine serves as a good measure for monitoring the anti-inflammatory effects of statins. For these reasons, among many others, it is of interest to the scientific and medical communities to better understand the role of tyrosine nitrosylation in normal and disease conditions of the body.

Sulfation has a well-established role in drug metabolism and chemical defense. In this regard, many chemicals to which we are exposed are rendered more biologically active following metabolism, and this bioactivation is central to the mechanism of action of numerous cancer-causing agents, including those in the diet. Sulfation is the terminal step in the bioactivation of numerous cancer-causing agents. To understand abnormal sulfation in the body, researchers are currently studying human genes for sulfation enzymes. As an example, studies have focused on the possibility that certain sulfation enzyme gene mutations can serve as risk factors in cancer of the bladder and colon, which represent target tissues for cancer-causing agents that are activated by sulfation. As an example of normal sulfation in the body, certain hormones such as catecholamines circulate predominantly as their sulfate conjugates (more than 95% of circulating dopamine is in the form of dopamine sulfate). An increased understanding of sulfation that occurs in normal and disease conditions is expected to provide further insight into drug metabolism and chemical defense, as well as into normal and disease conditions of the body.

Thus, detecting and isolating modified forms of molecules, such as proteins, is of interest to those doing research to understand normal and abnormal conditions of cells and systems of the body, as well as to those developing tests for diagnosis and prognosis of abnormal conditions relating to protein modifications.

Microorganisms often live in iron-limiting environments due to the very low solubilities of ferric hydroxide complexes under aerobic conditions at near neutral to slightly alkaline pH values (Atkinson et al, 1998). In the cells, tissues and body fluids of animals, free iron concentration is also maintained at very low levels through the activity of iron-sequestering proteins, such as transferrin and lactoferrin, suggesting that bacterial pathogenicity depends upon an ability to acquire iron form the host. In most all aerobic and facultative anaerobic microorganisms respond to low iron conditions by producing relatively low molecular weight ferric iron-chelating siderophores to aid them in acquiring iron from their environment (Neilands, 1995). Most of these microorganisms are known to synthesize at least one siderophore and hundreds of siderophores have been structurally characterized to date (Winkelmann, 1999). In 1963, desferrioxamine B (a.k.a. Desferal, deferoxamine, desferoxamine, desferroxamine, ferrioxamine), a siderophore obtained from *Streptomyces pilosus*, was introduced to the clinic for removal of excess iron resulting from the supportive therapy for beta-thalassemia. A variety of oral and parenteral iron chelating agents have been devised by the clinical research community since then, though desferroxamine B remains one of the more popular treatment modalities.

SUMMARY

The invention provides methods for isolating a target molecule from a sample. In an embodiment, the method involves contacting a sample with a capture agent, the agent comprising a siderophore and a transition metal cation, under conditions wherein the agent is capable of binding a target molecule to form a target molecule-capture agent complex, wherein the target molecule is selected from the group consisting of a phosphorylated molecule, a nitrotyrosine-containing molecule and a sulfated molecule, and separating the target molecule-capture agent complex from the sample, thereby isolating the target molecule from the sample. In one embodiment, the method can be used for isolating a phosphorylated molecule from a sample. In another embodiment, the method can be used isolating a nitrotyrosine containing molecule from a sample. In yet another embodiment, the method can be used for isolating sulfated molecule from a sample. The method can also include separating the target molecule from the target molecule-capture agent complex. A sample used in a solution.

The invention provides methods for determining the presence of a target molecule in a sample. In an embodiment, the method involves contacting a sample with a capture agent, the agent comprising a siderophore and a transition metal cation, under conditions wherein the agent is capable of binding a target molecule to form a target molecule-capture agent complex, wherein the target molecule is selected from the group consisting of a phosphorylated molecule, a nitrotyrosine-containing molecule and a sulfated molecule, and detecting formation of a target molecule-capture agent complex, thereby determining the presence of the target molecule in the sample. In one embodiment, the method can be used for determining the presence of a phosphorylated molecule in a sample. In another embodiment, the method can be used for determining the presence of a nitrotyrosine containing molecule in a sample. In yet another embodiment, the method can be used for determining the presence of a sulfated molecule in a sample.

The detecting can be performed, for example, by measuring binding between the capture agent and the target molecule. The measuring can include a mode selected from the group of absorbance, transmission, mass measurement, fluorescence intensity, fluorescence polarization, time-resolved fluorescence, resonance light scattering, surface-enhanced Raman scattering, inductively-coupled plasma mass spectrometry, electron paramagnetic resonance, refractive index absorbance, nuclear magnetic resonance, microcalorimetry, Fourier transform infrared spectrometry, atomic spectrometry, surface plasmon resonance, refractive index changes, spectropolarimetry and ellipsometry. In an embodiment, the siderophore portion of the target molecule-capture agent complex is detected. In another embodiment, the transition metal portion of the target molecule-capture agent complex is detected. In a further embodiment, a phosphorylated molecule portion of the target molecule-capture agent complex is detected.

In a specific embodiment, the invention method for isolating a phosphorylated molecule from a sample. The method involves contacting a sample with a capture agent, the agent comprising a siderophore and a transition metal cation, under conditions wherein the agent is capable of binding a phosphorylated molecule to form a phosphorylated molecule-capture agent complex, and separating the phosphorylated molecule-capture agent complex from the sample, thereby isolating the phosphorylated molecule from the sample.

The invention provides commercial packages. In one embodiment, the commercial package can contain an isolated siderophore and a transition metal salt. In another embodiment, the commercial package can contain an isolated siderophore and a transition metal solution. In a further embodiment, the siderophore can be attached to a support.

The invention provides a method for identifying a capture agent. The method involves contacting a siderophore-transition metal cation-complex with a phosphorylated moiety, and determining the ability of the complex to bind to the phosphorylated moiety, thereby identifying a capture agent. In an embodiment, the method further can involve contacting a siderophore with a transition metal cation, and determining the ability of the siderophore to bind to the transition metal cation, wherein a siderophore that binds to the transition metal cation is identified as a siderophore-transition metal cation-complex.

In another embodiment, the siderophore can be contacted with a transition metal cation in the presence of a detectable transition metal cation-binding substance, and the ability of the siderophore to displace the detectable transition metal cation-binding substance to form a siderophore-transitional metal cation complex is determined. The siderophore-transition metal cation-complex is contacted with a detectable phosphorylated moiety, if desired. Further, the ability of the complex to bind to the phosphorylated moiety can be determined by detecting hydrolysis of the detectable moiety. Exemplary detectable phosphorylated moieties include 6,8-difluoro-4-methylumbelliferyl and 4-nitrophenyl phospho.

In an embodiment of the methods of the invention for isolating a phosphorylated molecule from a sample, the sample can include a hydrophobic phase and a hydrophilic phase, and the method can involve contacting a sample with a capture agent, wherein the agent comprises a lipid soluble siderophore and a transition metal cation, under conditions wherein the agent is capable of binding a phosphorylated molecule to form a phosphorylated molecule-capture agent complex contained in a hydrophobic phase; contacting the phosphorylated molecule-capture agent complex with a lipophilic phosphorylated competitor compound to form a lipophilic phosphorylated competitor-capture agent complex; and collecting a hydrophilic phase, thereby isolating the phosphorylated molecule from the sample. The hydrophilic phase can be, for example, an aqueous phase. The siderophore can be, for example, an exochelin siderophore.

The invention provides another embodiment of the methods for isolating a target molecule from a sample. The method involves contacting a sample with a capture agent, the agent comprising a desferrioxamine siderophore and a gallium (III) cation, under conditions wherein the agent is capable of binding a target molecule to form a target molecule-capture agent complex, wherein the target molecule is selected from the group consisting of a phosphorylated molecule, a nitrotyrosine-containing molecule and a sulfated molecule, and separating the target molecule-capture agent complex from the sample, thereby isolating the target molecule from the sample.

Also provided is another embodiment of the methods for determining the presence of a target molecule in a sample. The method involves contacting a sample with a capture agent, the agent comprising a desferroxamine siderophore and a gallium (III) cation, under conditions wherein the agent is capable of binding a target molecule to form a target molecule-capture agent complex, wherein the target molecule is selected from the group consisting of a phosphorylated molecule, a nitrotyrosine-containing molecule and a sulfated molecule, and detecting formation of a target molecule-capture agent complex, thereby determining the presence of the target molecule in the sample. In an embodiment the sample can include a support, such as particle, bead, gel, matrix, membrane, filter or surface. Examples of surfaces include a microwell plate, MALDI-TOF target plate, array, microarray substrate, capillary, and microscope slide. A capture agent similarly can be attached to a surface.

DESCRIPTION

Figure 1:
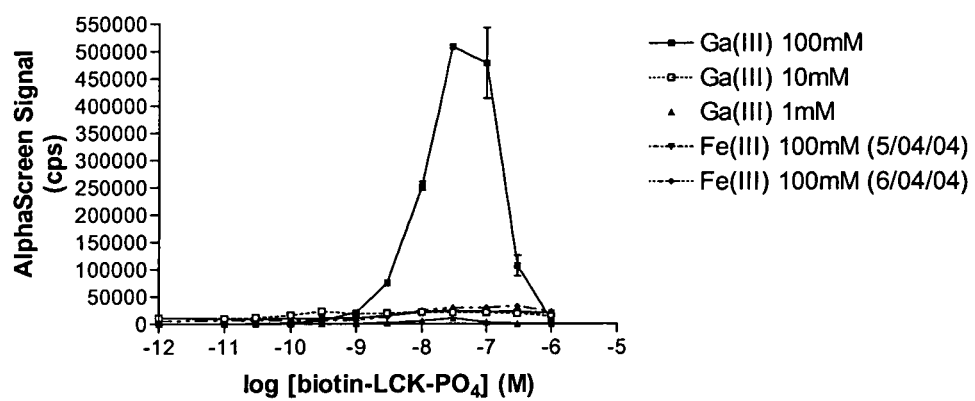
FIG. 1 shows detection of phosphopeptides using a capture agent that includes a siderophore coordinated with a transition metal cation.

The technology described herein relates to methods, compositions and commercial packages for isolating and/or detecting target molecules, such as phosphorylated molecules, nitrotyrosine-containing molecules and sulfated molecules.

In an embodiment, the present invention is directed to methods for isolating a target molecule, such as one containing one or more of a phosphorylated moiety, a nitrotyrosine moiety and a sulfated moiety, or a combination thereof. Isolation of a target molecule from a sample can be achieved by binding the target molecule to a capture agent and separating the target molecule-capture agent complex from the sample. The capture agent contains a siderophore coordinated with one or more transition metal ions, and the siderophore-transition metal ion complex provides selective binding to the target molecule. As is described below, a variety of siderophore-transition metal ion complexes are suitable for binding to target molecules. Example 6 describes use of a capture agent containing a desferrioxamine-gallium (III) complex for selectively binding to phosphopeptides, phosphoinositides, sulfated molecules and nitrotyrosine-containing molecules. Once a target molecule-capture agent complex is formed, it can be removed from the sample by a variety of means, depending on the format selected by the user. For example, when the capture agent is attached to a support, separation can be performed by separating the support (solid or semi-solid phase) from the sample (liquid phase), or visa versa. As another example, when the capture agent contains an isolation tag such as an epitope recognized by an antibody or other binding partner, separation can be performed by binding the capture agent portion of the target molecule-capture agent complex to the isolation tag and collecting isolation tag-bound complexes. A variety of well known procedures for collecting molecular complexes can be used within the context of the methods described herein.

In another embodiment, the present invention is directed to methods for detecting a target molecule, such as a target molecule containing one or more of a phosphorylated moiety, a nitrotyrosine moiety or a sulfated moiety, or a combination there. Detection of a target molecule in a sample can be achieved by binding the target molecule to a capture agent and detecting the target molecule-capture agent complex, or a portion of the complex. As is described herein below numerous and diverse analytical methods can be applied to detecting such a complex or a portion of the complex. For example, one component of the complex can be labeled with a detectable tag, and the presence of the tag in an isolated complex can be detected. As another example, a physiochemical property of a complex relative to its components, such as mass, can be detected. As an additional example, a property resulting from the proximity between target molecule and capture agent when complexed, such as fluorescence resonance energy transfer, can be detected. Example 6 describes detecting femtomolar amounts of phosphopeptides, phosphoinositides, sulfated molecules and nitrotyrosine-containing molecules using a capture agent containing a desferrioxamine-gallium (III) complex in a proximity assay format.

The technology described herein involves binding of a target molecule to a capture agent that contains a siderophore coordinated with a transition metal cation. The target molecule generally binds to the transition metal cation portion of the capture agent, but also can bind to both the siderophore and transition metal cation, depending on the particular capture agent and target molecule involved. Previous studies have shown that phosphoproteins can bind to metal ions. As such, phosphoprotein detection and purification products are available commercially, including the IMAC (immobilized metal ion affinity chromatography) assay (Molecular Devices, Sunnyvale, Calif.), the Pro-Q Diamond phosphoprotein gel stain (Molecular Probes, Eugene, Oreg.) and the ZipTipMC Pipette Tips (Millipore Corporation, Billerica, Mass.). These products involve use of trivalent transition metal cations coordinated with a synthetic small molecule organic chelate, such as imminodiacetate, nitrilotriacetate, 1,4,7-triazocyclononane or 1,2-bis (2-aminophenoxy) ethane-N,N,N'N'-tetraacetic acid (BAPTA). Isolation of phosphorylated molecules using these techniques are generally performed at acidic pH values of 3 to 6. Gabreicevic and Crumbliss hypothesize that such low pH is needed because the small molecule organic chelators fail to bind phosphorylated molecules at neutral pH due to their reduced capability to bind the transition metal cations at these higher pH values (Gabricevic and Crumbliss, 2003). In contrast, the methods described herein for detecting and isolating a target molecule can be performed at or near neutral pH, if desired.

As used herein, the term "target molecule" means a molecule that is capable of binding selectively to a given siderophore-transition metal cation complex. The term "target molecule" encompasses any type of molecule that contains a covalently bound or non-covalently bound phosphorylated moiety, nitrotyrosine moiety, sulfated moiety. Non-limiting examples of molecules that can contain a phosphorylated moiety include an amino acid, a peptide, a polypeptide, a nucleotide, a polynucleotide, a lipid, and a carbohydrate. Non-limiting examples of molecules that can be sulfated include a carbohydrate, such as a saccharide, a glycolipid, a glycosamine glycan, and the like. Non-limiting examples of molecules that can contain a nitrotyrosine include the amino acid tyrosine, any polypeptide or peptide that contains a tyrosine residue, and any fusion or artificial molecule that incorporates a tyrosine residue. A target molecule can be bound to one or more other molecules, or can be a singular molecule. Selective binding means that the capture agent binds to one or more phosphomolecule, nitrotyrosine-containing molecule, and/or sulfated molecule but does not substantially bind to non-phosphomolecules, non-nitrotyrosine-containing molecules or non-sulfated molecules, or other unrelated molecules. It is understood that a particular capture agent used in a method or commercial package of the invention can be capable of specific binding to phosphomolecules, nitrotyrosine-containing molecules, and sulfated molecules simultaneously, or to a subset of these types of molecules, including specific binding selectively to phosphomolecules, selectively to nitrotyrosine-containing molecules, and selectively to sulfated molecules. Example 6 describes a desferrioxamine-gallium (III) cation capture agent having specific binding to phosphomolecules, nitrotyrosine-containing molecules and sulfated molecules.

As used herein, the term "capture agent" means an entity capable of binding selectively to a target molecule. A capture agent includes a siderophore coordinated with one or more transition metal cations. The siderophore portion of the capture agent can be complexed with a ligand in addition to transition metal cations, if desired. A capture agent can also contain a tag, which can be attached to or inherently present in the siderophore portion or transitional metal cation portion of the capture agent.

As used herein, the term "siderophore" means an organic molecule that is capable of coordinating transition metal cations. Siderophores include naturally occurring molecules produced by a variety of organisms, including microbes, such as prokaryotes and fungi, plants and higher organisms. Siderophores also include modified, artificial or man-made molecules such as tagged forms of naturally occurring siderophores, so long as the siderophore retains the ability to coordinate transition metal cations. A siderophore can have a chemical structure categorized within well known siderophore structural classes. Exemplary structural classes of siderophores include hydroxamate siderophores, catechol siderophores, and phenolate-based siderophores. Non-limiting examples of hydroxamate siderophores include ferrichrome, ferrirubin, rhodotorulic acid, triacetylfusarinine, ferricrocin, exochelins, vicibactin, dimerum acid, acetyl dimerum acid, schizokinen, coprogen B, methyl coprogen B, fusarinine, acinetoferrin, ornibactins, amphibactins, marinobactins, aquachelins, mycobactins and desferrioxamine. Non-limiting examples of catecholate siderophores include chrysobactin, enterobactin, the spermidine-based catechol siderophore-carbacephalosporin (JAM-2-263), the N5-acetyl-N5-hydroxy-L-ornithine tripeptide hydroxamate siderophore-carbacephalosporin (EKD-3-88), azotobactin delta, a naturally fluorescent siderophore that contains a catecholate-type group within the chromophore and an alpha- hydroxycarboxylic acid group in the middle of the peptide chain and a terminal hydroxamate group, IC202A (a ferrioxamine-related compound containing a butylidene N-oxide function as described in Iijima et al. (1999) *J Antibiot* (Tokyo). 52(1):25-8, and Iijima et al. (1999) *J Antibiot* (Tokyo) 52(1):20-4), and exochelins. Non-limiting examples of phenolate-based siderophores include pyochelin, and alcaligin E.

A siderophore can also have a chemical structure different from well known siderophore structural classes. Exemplary siderophores of this type include a siderophore isolated from *Rhizobium melioti* that contains ethylenediaminedicarbonyl and α-hydroxycarbonyl functional groups for iron binding (Smith M J. and Neilands J B. (1984) *J. Plant Nutr.* 7: 449-458). Man-made or artificial siderophores generally have chemical structures based on those of known siderophores and combinations of siderophores. Exemplary artificial hydroxamate and catechole class siderophores are described, for example, in Heggemann et al. (2003) *Biometals*. 16(4): 539-51 and Slomczynska et al. (2000) *Transfus Sci.* 23(3): 265-6, which are incorporated herein by reference. Artificial mixed mono- or biscatecholate hydroxamates are described, for example, in Szarapinska-Kwaszewska et al. (2003) *Acta Microbiol Pol.* 52(3):261-9, which is incorporated herein by reference.

A siderophore can be naturally luminescent, or chemically modified to be luminescent. In particular, a siderophore useful in various embodiments of the technology described herein is a fluorescent siderophore. Exemplary naturally fluorescent siderophores include azotobactin, mycobactin, azoverdin, pyroverdin PaA, pseudobactin B10, pyroverdin GM-II, pyroverdin G4A, pyroverdin G4R or succinopyroverdin. Exemplary chemically modified siderophores include 7-nitro-2,1,3-benzoxadiazol-4-yl, N-methylanthranyl or 2-cyanonaphtho[2,3-c]-2H-pyrrolyl desferrioxamine, as well as 7-(9'-anthracenyl)-5-oxo-2-oxa-6-azaheptyl ferrichrome.

A siderophore can be capable of coordinating with one or more transition metal cations, such as iron(III), gallium (III), indium (III), aluminum (III), cerium (III), yttrium (III), zirconium (IV), titanium (IV), and copper(II), zinc (II), tantalum (V). The affinity of siderophores for gallium ions is generally high, while their affinity for monovalent and divalent cations is relatively low (Folschweiller N, Gallay J, Vincent M, Abdallah M A, Pattus F, Schalk I J. (2002) Dec 10;41(49): 14591-601; Wasielewski et al, Biochemistry. 2002 Oct 15;41 (41):12488-97; Moberg et al, Anal Chem. 2004 Can 1;76(9): 2618-22). However, as is described herein below, a siderophore coordinated with a copper (II) transition metal cation can be useful for detecting and/or isolating a target molecule containing phosphorylated histidine. Methods for determining the ability of a siderophore to coordinate with a particular transition metal ion are well known to those skilled in the art and are exemplified herein below. Such methods can be used for determining the ability of a transition metal cation such as one listed above, as well as other cations, such chromium, lead, manganese, cadmium, scandium, vanadium, ruthenium (III) and europium (III), to coordinate with a selected siderophore.

Though nominally siderophores bind to iron (III) in a one to one stoichiometry, it is possible to load higher amounts of certain transition metal cations into the structure of certain siderophores, which can be advantageous for isolating and detecting phosphorylated compounds. Additionally, some siderophores do not provide full one to one coordination of transition metal cations, such as Fe(III), which is also of benefit in terms of isolating and detecting phosphorylated compounds. Examples of variations in siderophore/metal cation stoichiometry are as follows. Alcaligin and bisucaberin are known to form one to one ferric ion/siderophore complexes at acidic pH values, but two to three complexes at pH values slightly about neutrality (Hou et al, 1998). At even higher pH values, a two to two complex forms. Chrysobactin is unable to provide full one to one coordination of ferric ions and the stoichiometry in aqueous solution also varies depending upon solution pH (Persmark and Neilands, 1992). Variations in the ligation of the metal cation/siderophore complex can be exploited to facilitate creation of the ternary phosphorylated compound/metal cation/siderophore complex. The objective is to provide some coordination sites on the transition metal cation that are occupied by labile aquo ligands which are amenable to displacement by the phosphate moiety of the target phosphorylated compound, while the other sites are occupied by strong ligands derived from the siderophore. Finally, additives, such as inorganic salts, alcohols. detergents or surfactants, may be included in the solution containing phosphorylated compound, transition metal cation and siderophore or siderophore-like molecule in order to promote or stabilize formation of the ternary complex.

A specific type of siderophore described herein is a desferrioxamine. Desferrioxamine has been used clinically to remove iron from the body of a patient. During such use it has been observed that desferrioxamine can also remove aluminum from the body. A variety of desferrioxamine forms are commercially available, including for example, Desferal™, desferrioxamine mesylate salt, deferoxamine methanesulfonate salt, 7-nitrobenz-2-oxa-1,3-diazole desferrioxamine B, N-hydroxydesferrioxamine B. A variety of modified forms of desferrioxamines have been identified. Preparation of artificial desferrioxamines including non-amide analogues, C-terminal modified analogues, reverse-amide analogues, and hybrid analogues is described, for example, in Poreddy et al, *J Comb Chem*. (2004) 6(2):239-54, which is incorporated herein by reference. As desferrioxamine family members have highly related chemical structures, it will be recognized that any desferrioxamine family member complexed with a suitable transition metal ion will be capable of binding selectively to a target molecule. As used herein, the terms "a desferrioxamine" and "a desferrioxamine family member" mean a known desferrioxamine molecule, including any of those described herein above, and any modified form of a known desferrioxamine molecule so long as the modified form retains the ability to coordinate with a transition metal cation, such as gallium (III).

As used herein, the term "target molecule" means a molecule to which a capture agent selectively binds. A target molecule contains phosphorylated moiety, a nitrotyrosine moiety, a sulfated moiety, or a combination thereof. A target molecule can be bound to one or more other molecules, or can be a singular molecule. Selective binding means that the capture agent binds to one or more phosphomolecule, nitrotyrosine-containing molecule, and/or sulfated molecule but does not substantially bind to non-phosphomolecules, non-nitrotyrosine-containing molecules or non-sulfated molecules, or other unrelated molecules. It is understood that a particular capture agent used in a method or commercial package of the invention can be capable of selective binding to phosphomolecules, nitrotyrosine-containing molecules, and sulfated molecules simultaneously, or to a subset of these types of molecules, including binding selectively to phosphomolecules, selectively to nitrotyrosine-containing molecules, and selectively to sulfated molecules. Example 6 describes a desferrioxamine-gallium (III) cation capture agent having selective binding to phosphomolecules, nitrotyrosine-containing molecules and sulfated molecules.

As used herein, the term "support" means a solid or semisolid material to which a capture agent can be attached, or which can be functionalized to include a capture agent. For example, a support can be a natural or synthetic polymer, resin, metal or silicate. A support also can be a biological material such as a virus; a virus like particle, for example a bacteriophage; a bacterium, for example, *E. coli*; a eukaryotic cell for example a yeast, insect or mammalian cell. Suitable supports are known in the art and illustratively include an agarose, such as is commercially available as Sepharose; a cellulose, illustratively including a carboxymethyl cellulose; a dextran, such as is commercially available as Sephadex; a polyacrylamide; a polystyrene; a polyethylene glycol; a resin; a silicate; divinylbenzene; methacrylate; polymethacrylate; glass; ceramics; paper; metals; metalloids; polyacryloylmorpholide; polyamide; poly(tetrafluoroethylene); polyethylene; polypropylene; poly(4-methylbutene); poly(ethylene terephthalate); rayon; nylon; poly(vinyl butyrate); polyvinylidene difluoride (PVDF); silicones; polyformaldehyde; cellulose acetate; nitrocellulose; mixtures thereof, and the like. A support useful in a method of the invention can have a variety of physical formats, which can include for example, a membrane, column, a hollow, solid, semi-solid, pore or cavity containing particle such as a bead, a gel, a fiber, including a fiber optic material, a matrix and sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. A particle to which a capture agent is attached can have a variety of sizes, including particles that remain suspended in a solution of desired viscosity, as well as particles that readily precipitate in a solution of desired viscosity. If desired, a support can include a tag, such as a tag useful for detection and/or purification.

As used herein, the term "isolating" when used in reference to a target molecule, means the act of separating the target molecule from other molecules, substances or materials in the sample. The term "isolated" when used in reference to a target molecule, capture agent, siderophore or other component useful in a method or commercial package of the invention means that the component is acted upon by the hand of man to remove other molecules, substances or materials with which the component is associated in a sample or preparation. The term isolated does not require absolute purity, but rather is intended as a relative term.

As used herein, the term "selective" when used in reference to the interaction or binding between a capture agent or siderophore-transition metal ion complex and a target molecule, means that non-target molecules do not substantially bind to the capture agent or siderophore-transition metal ion complex.

As is described herein, a capture agent containing a siderophore coordinated with a transition metal cation can bind selectively to a target molecule, and therefore can be useful for isolating a target molecule. Therefore, the invention provides a method for isolating a target molecule from a sample. The method involves (a) contacting a sample with a capture agent, the agent comprising a siderophore and a transition metal cation, under conditions wherein the agent is capable of binding a target molecule to form a target molecule-capture agent complex, and (b) separating the target molecule-capture agent complex from the sample, thereby isolating the target molecule from the sample. The target molecule can be, for example, a phosphorylated molecule, a nitrotyrosine-containing molecule, a sulfated molecule or a molecule having a combination of phosphorylation, nitrotyrosine and/or sulfation. The sample can be in solution or contained on a support. In an embodiment, the siderophore can be a naturally occurring siderophore, such as a prokaryotic siderophore and a fungal siderophore, and can be a tagged form of such siderophores.

In an embodiment, a capture agent used in a method of the invention can be selective for a phosphorylated molecule. Therefore, in a specific embodiment, the invention provides a method for isolating a phosphorylated molecule from a sample, comprising (a) contacting a sample with a capture agent, the agent comprising a siderophore and a transition metal cation, under conditions wherein the agent is capable of binding a phosphorylated molecule to form a phosphorylated molecule-capture agent complex, (b) separating the phosphorylated molecule-capture agent complex from the sample, thereby isolating the phosphorylated molecule from the sample.

In another embodiment, a capture agent used in a method of the invention can be selective for a nitrotyrosine-containing molecule. Thus, in another specific embodiment, the invention provides a method for isolating a nitrotyrosine-containing molecule from a sample, comprising (a) contacting a sample with a capture agent, the agent comprising a siderophore and a transition metal cation, under conditions wherein the agent is capable of binding a nitrotyrosine-containing molecule to form a nitrotyrosine-containing molecule-capture agent complex, (b) separating the nitrotyrosine-containing molecule-capture agent complex from the sample, thereby isolating the nitrotyrosine-containing molecule from the sample.

In a further embodiment, a capture agent used in a method of the invention can be selective for a sulfated molecule. Accordingly, in a further specific embodiment, the invention provides a method for isolating a sulfated molecule from a sample, comprising (a) contacting a sample with a capture agent, the agent comprising a siderophore and a transition metal cation, under conditions wherein the agent is capable of binding a sulfated molecule to form a sulfated molecule-capture agent complex, (b) separating the sulfated molecule-capture agent complex from the sample, thereby isolating sulfated molecule from the sample.

As is described herein, a capture agent containing a siderophore and transition metal cation can be useful for detecting a target molecule, such as a phosphorylated molecule, nitrotyrosine-containing molecule, and a sulfated molecule. Therefore, the invention provides a method for determining the presence of a target molecule in a sample. The method involves (a) contacting a sample with a capture agent, the agent comprising a siderophore and a transition metal cation, under conditions wherein the agent is capable of binding a target molecule to form a target molecule-capture agent complex, (b) detecting formation of a target molecule-capture agent complex, thereby determining the presence of the target molecule in the sample.

In a specific embodiment, the invention provides a method for determining the presence of a phosphorylated molecule in a sample. The method involves (a) contacting a sample with a capture agent, the agent comprising a siderophore and a transition metal cation, under conditions wherein the agent is capable of binding a phosphorylated molecule to form a phosphorylated molecule-capture agent complex, and (b) detecting formation of a phosphorylated molecule-capture agent complex, thereby determining the presence of a phosphorylated molecule in the sample.

In another specific embodiment, the invention provides a method for determining the presence of a nitrotyrosine-containing molecule in a sample. The method involves (a) contacting a sample with a capture agent, the agent comprising a siderophore and a transition metal cation, under conditions wherein the agent is capable of binding a nitrotyrosine-containing molecule to form a nitrotyrosine-containing molecule-capture agent complex, and (b) detecting formation of a nitrotyrosine-containing molecule-capture agent complex, thereby determining the presence of a nitrotyrosine-containing molecule in the sample.

In a further specific embodiment, the invention provides a method for determining the presence of a sulfated molecule in a sample. The method involves (a) contacting a sample with a capture agent, the agent comprising a siderophore and a transition metal cation, under conditions wherein the agent is capable of binding a sulfated molecule to form a sulfated molecule-capture agent complex, and (b) detecting formation of a sulfated molecule-capture agent complex, thereby determining the presence of a sulfated molecule in the sample.

A target molecule can be isolated and/or detected from a variety of types of samples using the technology described herein. As used herein, the term "sample" means a substance that contains or is suspected of containing a target molecule. A sample useful in a method of the invention for isolating and/or detecting a target molecule can be a liquid or solid, can be dissolved or suspended in a liquid, can be in an emulsion or gel, and can be bound to or absorbed onto a material. A sample can be a biological sample, environmental sample, experimental sample, diagnostic sample, or any other type of sample that contains or is suspected to contain a target molecule. As such, a sample can be, or can contain, an organism, organ, tissue, cell, bodily fluid, biopsy sample, or fraction thereof.

The compositions and methods described in this disclosure can be performed on samples that are immobilized on a solid or semisolid substrate, such as a gel, a membrane, a bead, a MALDI-TOF target plate, the surface of a microwell plate, a capillary wall or a microarray surface. Alternatively, they can be performed on samples that are in solution, such as within a microwell plate, cuvette, test tube, capillary or microfluidic device. The sample is defined to include any material that is suspected to contain phosphorylated compounds, including substrates of kinases and phosphates. In a biological context, these might typically be biological fluids, whole organisms, organs, tissues, cells, culture supernatants, subcellular organelles, protein complexes, individual proteins, recombinant proteins, fusion proteins, viruses, viral particles, peptides or amino acids. Unfractionated samples can be directly subjected to the analysis or alternately samples that have been fractionated by a variety of techniques, such as immunoprecipitation, 1-D gel electrophoresis, 2-D gel electrophoresis, electroblotting, liquid chromatography, electrochromatography, dialysis, two-phase polymer separations and solid phase extraction may be evaluated.

A sample can be processed to preserve or stabilize target molecules. Methods for preserving the integrity of molecules in a sample are well known to those skilled in the art. Such methods include the use of appropriate buffers and/or inhibitors, including nuclease, protease and phosphatase inhibitors that preserve or minimize changes in the molecules in the sample. Such inhibitors include, for example, chelators such as ethylenediamne tetraacetic acid (EDTA), ethylene glycol bis(P-aminoethyl ether)N,N,N1,NI-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for allowing selective interactions between molecules are well known to those skilled in the art and can be varied depending, for example, on the type of molecule in the sample to be characterized (see, for example, Ausubel et al., *Current Protocols in Molecular Biology* (Supplement 47), John Wiley & Sons, New York (1999); Harlow and Lane, *Using Antibodies: A Laboratory Manual*, Cold Spring Harbor Press (1999); Tietz *Textbook of Clinical Chemistry*, 3rd ed., Burtis and Ashwood, eds., W. B. Saunders, Philadelphia, (1999)). A sample also can be processed to reduce the presence of interfering substances and/or reduce non-selective binding of sample components to a capture agent. For example, a tendency of acidic polypeptides to bind to a capture agent non-selectively can be reduced by methyl esterification of the polypeptide sample (Ficarro et al, 2002; Brill et al, 2004).

Various methods for fractionating a fluid sample or cell extract are well known to those skilled in the art, including subcellular fractionation or chromatographic techniques such as ion exchange, hydrophobic and reverse phase, size exclusion, affinity, hydrophobic charge-induction chromatography, and the like (Ausubel et al., supra, 1999; Scopes, *Protein Purification: Principles and Practice*, third edition, Springer-Verlag, New York (1993); Burton and Harding, *J. Chromatoqr.* A 814:71-81 (1998)).

A target molecule detected, isolated or otherwise acted upon in accordance with a method of the invention can have a variety of structural and physiochemical properties so long as the molecule is capable of binding to a capture agent as described herein. Target molecules include phosphorylated molecules, nitrotyrosine containing molecules, sulfated molecules and molecules having similar, mimetic and modified forms of phosphorylated moieties, nitrotyrosine moieties and sulfated moieties.

In an embodiment, the methods and compositions of the invention are useful for detecting and isolating phosphorylated molecules. The phosphorylated moiety on the molecules can be a covalent modification of the molecule itself and can be a phosphorylated moiety on a molecule that is non-covalently bound to the target molecule. A phosphorylated moiety on a target molecule can be naturally occurring or non-physiological. A variety of molecules can be phosphorylated under natural and/or non-physiological conditions. Non-limiting examples of such molecules include an amino acid, a peptide, a protein, a nucleotide, a polynucleotide, a lipid and a carbohydrate.

In a specific embodiment, a phosphorylated molecule detected and/or isolated using a method of the invention is a phosphorylated polypeptide. Examples of molecules that bind non-covalently to polypeptides and have phosphorylated moieties include nucleotide triphosphates, nucleotide diphosphates and phosphoinositides. Examples of phosphorylated molecules include phosphorylated amino acids such as serine, threonine, tyrosine, 1-phosphohistidine, 3-phosphohistidine, phosphoaspartic acid, phosphoglutamic acid, N epsilon-phospholysine, delta-O-phosphohydroxylysine, N omega-phosphoarginine and phosphocysteine. Examples of non-physiological phosphoryated moieties include a thiophosphorylated moiety, O-boranophosphorylated moiety, O-dithiophosphorylated moiety, as well as phosphoramide, H-phosphonate, alkylphosphonate, phosphorothiolate, phosphodithiolate, phosphorofluoridate and the like.

In an embodiment, the methods and compositions of the invention are useful for detecting and isolating nitrotyrosine-containing molecules. The nitrotyrosine moiety on the target molecule can be a covalent modification of the molecule itself and can be a nitrotyrosine moiety on a molecule that is non-covalently bound to the target molecule. A nitrotyrosine moiety on any target molecule can be naturally occurring or non-physiological. In an embodiment, the methods of the invention can be used to detect nitrotyrosine-containing polypeptides. The methods can be applied to detecting specific nitrotyrosine-containing polypeptides, such as those known or suspected to contain nitrotyrosine under a particular cell condition, as well as to detecting uncharacterized nitrotyrosine-containing peptides.

In an embodiment, the methods and compositions of the invention are useful for detecting and isolating sulfated molecules. The sulfated moiety on the molecule can be a covalent modification of the molecule itself and can be a sulfated moiety on a molecule that is non-covalently bound to the target molecule. Numerous highly charged sulfated molecules, including sulfated glycosaminoglycans, are known to exist in nature and found to possess interesting physiological roles. Several mycobacteria, including human pathogenic mycobacteria, are known to produce sulfated compounds such as glycolipid and glycopeptidolipid, that are suspected of having roles in bacterial pathogenesis. Other sulfated molecules, including sulfated saccharides, bacterial metabolites and eukaryotic molecules can be detected and isolated according to a method described herein.

A sulfated moiety on any target molecule can be naturally occurring or non-physiological. In an embodiment, the methods of the invention can be used to detect a sulfated glycosaminoglycan, a sulfated lipid, a sulfated glycopeptidolipid, a sulfated saccharide and a sulfated polypeptide. A specific example of a glycosaminoglycan is a heparin.

A capture agent useful in the methods and compositions of the invention contains a siderophore coordinated with one or more transition metal cations. A capture agent can contain more than one siderophore, including more than one of the same type of siderophore and two or more different siderophores, if desired. The capture agent can also include a support, tag, or other component that alters the physical properties of the capture tag in a desirable manner. For example, a capture agent can include a component that allows it to be isolated or detected, that alters its hydrophobic or solubility characteristics, that improves its stability, that alters its charge or mass, and the like.

A siderophore present in a capture agent can be selected based on its ability to bind to one or more specific types of target molecules under particular conditions. As is described in Example 6, a desferrioxamine siderophore coordinated with gallium (III) cation can be used for detecting or isolating a phosphorylated target molecule, a nitrotyrosine-containing target molecule and a sulfated target molecule. Therefore, in an embodiment, a capture agent contains a desferrioxamine family siderophore, such as desferrioxamine. In a specific embodiment, the desferrioxamine is complexed with a gallium (III) cation. In another embodiment, a capture agent contains a mixed catecholate-hydroxamate siderophore, such as a pyroverdin family siderophore. In specific embodiments, the pyroverdin family siderophore can be selected from azotobactin, mycobactin, pyroverdin PaA, pseudobactin B10, azoverdin, pyroverdin GM-II, pyroverdin G4A, pyroverdin G4R, and succinopyroverdin. A12. In an embodiment, the siderophore is a hydroxamate siderophore, such as a dessferrioxamine family siderophore and a ferrichrome family siderophore. A specific ferrichrome family siderophore is ferrichrome. In an embodiment, the siderophore is lipid-soluble. In a specific embodiment, the lipid-soluble siderophore is an exochelin siderophore. In yet another embodiment, the siderophore is selected from the group of ferrichrome, ferrirubin, schizokinen, rhodotorulic acid, triacetylfusarinine, ferricrocin, exochelins, vicibactin dimerum acid, acetyl dimerum acid, alcalgin E, pyochelin, coprogen B, methyl coprogen B, fusarinine, acinetoferrin, ornibactins, amphibactin, marinobactin, aquachelin, mycobactin, chrysobactin, cepabactin, pyoverdine, enterobactin, carbacephalosporin JAM-2-263, carbacephalosporin EKD-3-88 and azotobactin.

A capture agent including a siderophore coordinated with complex copper (II) ions can be used for selective detection and/or isolation of molecules containing phosphorylated histidine residues. Exemplary siderophores useful for this purpose include schizokinen and ferrioxamine B, which chelate copper (II) cations (McKnight and Morel, Liminol. Oceanogr. 1979 24: 823-837; McKnight et al. Liminol. Oceanogr. 1980 25: 62-711980; Arceneaux et al, Antimicrob Agents Chemother. 1984 Can;25(5):650-2; Clarke et al, Appl Environ Microbiol. 1987 Can;53(5):917-22). As is described in Napper et al. *Anal Chem.* 2003 Apr 1;75(7):1741-7, phosphorylated histidine containing peptides can be isolated using ZipTipMC pipet tips coordinate metal ions at neutral pH values is an advantage for the isolation and detection of histidine-phosphorylated peptides and proteins, relative to conventional organic chelators utilized in IMAC procedures because phosphate-histidine linkages are acid-labile and thus can be difficult to preserve under experimental conditions. As an example of a procedure for fluorescent moiety-labeled siderophore coordinated with copper (II) can be used in combination with cyanine 5 dye-labeled siderophore coordinated with gallium (III) to discriminate between phosphohistidine-containing and phosphomonoester-containing peptides on microarray. Unsulfonated versions of the cyanine dyes can be used in this application to minimize nonspecific labeling through binding to protein or peptide primary amine residues. Although copper (II) can quench certain siderophores, this quenching is generally orders of magnitude smaller than that generated by iron (III) itself. Therefore, in an embodiment of the invention, a siderophore coordinated with copper (II) cations can be used for detecting or isolating a phosphorylated histidine-containing molecule.

In an embodiment, a method of the invention employs a capture agent containing an exochelin siderophore. Exochelins are hydroxamate-class siderophores of *Mycobacterium tuberculosis* that are lipid soluble and hence able to enter cells (Dong and Miller, 2002 J Org Chem. Jul 12;67(14):4759-70). Lipid-soluble exochelins are suitable siderophores for the isolation of hydrophilic phosphopeptides by phase-partitioning procedures. When the phosphopeptides are complexed to the cation-charged siderophore, the hydrophobicity of the resulting complex is greater than that of the phosphopeptides alone, as well as the unbound nonphosphorylated peptides. In a two-phase extraction system based upon hydrophobicity, this will result in the phosphopetides being driven into the more hydrophobic phase and away from the bulk peptides in the system. Subsequently, the hydrophobic phase can be removed and mixed with fresh aqueous phase. Then a lipophilic phosphorylated compound, such as phenyl phosphate or 2-(thiophene-3-yl ethyl) phosphonic acid can be added in order to elute the phosphopeptides from the exochelin, and effect their subsequent recovery in the aqueous phase. Similar methods can be performed for detecting and/or isolating nitrotyrosine-containing molecules and sulfated molecules.

A capture agent useful in a method, composition or commercial package of the invention can be tagged. The tag can be present on a siderophore portion of a capture agent, a transition metal cation portion of the capture agent, or both portions. A capture agent can contain more than one tag, if desired. One type of tag is a hapten, such as biotin, digoxigenin, 2,4-dinitrophenol, 2,4-diclorophenoxyacetic acid, 4-ethoxymethylene-2-phenyl-2-oxazoline-5-one, and 5-benzimidazolecarboxylic acid. For example, in the case of a biotin-labeled capture agent, formation of a target molecule-biotin-labeled capture agent can be detected using a detectable avidin or streptavidin. In an embodiment, a siderophore portion of a capture agent is tagged. In a specific embodiment, the tag is a hapten, such as a hapten listed above. Another type of tag is a polypeptide that is detectable due to a physiochemical property, such as fluorescence, luminescence, and phosphorescence, or that can be rendered detectable, for example, due to its functional activity, such as an enzyme. A specific type of polypeptide tag is an enzyme, such as horse radish peroxidase, beta-galactosidase, and beta-glucuronidase. As an example, a capture agent can be tagged with horse radish peroxidase. Upon formation of a target molecule-capture agent complex, detection can then be performed using any of a wide range of well known methods for detecting horseradish peroxidase, including 3,3',5,5'-tetramethylbenzidine (TMB)-based chromogenic methods, 3,3'-diaminobenzidine tetrahydrochloride (DAB)-based chromogenic methods, 3-amino-9-ethylcarbazole (AEC)-based chromogenic methods, Amplex Red dye-based fluorogenic methods, enhanced luminol-based chemiluminescence reactions, electron paramagnetic resonance-based detection of free tyrosyl radical, luminescent semiconductor crystal (quantum dot) or tyramide signal amplification. Such detection methods are suitable for any enzyme having a known and detectable substrate. Another specific type of polypeptide tag is a photoprotein. As used herein, the term "photoprotein" means a polypeptide capable of emitting light. A photoprotein tag useful in a method of the invention can be naturally occurring or made-made. An exemplary photoprotein is a fluorescent polypeptide. Fluorescent polypeptides, such as phycobiliproteins, green fluorescent protein, yellow fluorescent protein, red fluorescent protein, obelin, aequorin, and Photina™, and variants thereof, can be detected when present in a target molecule-capture agent complex. Attachment of a photoprotein to a capture agent can be performed chemically, non-covalently and by standard molecular biology fusion tagging approaches.

Additional types of tags that can be employed in methods described herein include detectable moieties, such as luminescent moieties, fluorescent moieties, radioactive moieties and the like; purification tags such as polyhistidine, flag, myc and GST tags; polynucleotide tags, aptamers, protein nucleic acids; biological tags such as phage; antibody and antibody-like tags; mass tags such as particles of defined size, for example, metal beads and nanoparticle tags, and the like. In an embodiment, a method of the invention for isolating a target molecule and a method of the invention for detecting a target molecule can employ a siderophore tagged with a detectable moiety. The detectable moiety can be, for example, a fluorescent moiety. In a specific embodiment, the siderophore is a desferrioxamine. The desferrioxamine can contain a moiety such as fluorescein, rhodamine, 7-nitro-2,1,3-benzoxadiazol-4-yl, N-methylanthranyl and 2-cyanonaphtho[2,3-c]-2H-pyrrolyl. In another specific embodiment, the siderophore is a ferrichrome. The ferrichrome can contain a moiety such as fluorescein, rhodamine and 7-(9'-anthracenyl)-5-oxo-2-oxa-6-azaheptyl.

A tag can be attached to a capture agent, sample, or portion or component thereof, using a variety of well known chemical and biosynthetic methods. The particular procedure used will depend on the portion of the capture agent or sample to which the tag is attached, and the physicochemical properties of the selected tag. As an example relating to capture agents, bifunctional cross-linking agents can be incorporated into the capture agent, for example in the siderophore portion of the capture agent, in order to create reactive groups, such as N-hydroxysuccinimide (NHS), iodoacetamide and maleimide, that can subsequently be used to attach the capture agent to a tag.

In an embodiment of the methods, compositions and commercial packages of the invention, the capture agent can be presented to the target molecule whilst attached to a support. Alternatively, the support can be provided during or after the capture agent is presented to the target molecule, so long as the support is capable of selective attachment to the capture agent. Therefore, a support to which a capture agent is attached can be provided at any convenient point while practicing a method of the invention.

A capture agent can be attached to a support using a variety of well-known functional groups capable of interacting with a capture agent or portion thereof, to attach it to the support, while leaving the transition metal cation available to bind a target molecule. It is understood that in certain cases, a target molecule binds to both a transition metal cation and siderophore to form a target molecule-capture agent complex. A sample also can be attached to a support using such well-known functional groups. Illustrative examples of functional groups include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity.

A siderophore transition metal cation complex useful in a method or commercial package of the invention can be prepared under a variety of conditions to obtain a complex having desired characteristics. One characteristic is the particular metal cation selected. Methods for determining the ability of a particular metal cation to complex with a siderophore are well known to those skilled in the art, and are exemplified herein below. Another characteristic is the siderophore-transition metal cation stoichiometry. Examples of variations in siderophore/metal cation stoichiometry are as follows. Alcaligin and bisucaberin are known to form one to one ferric ion/siderophore complexes at acidic pH values, but two to three complexes at pH values slightly above neutrality (Hou et al, *Inorg Chem.* 1998 Dec 28;37(26):6630-6637). At even higher pH values, a two to two complex forms. Chrysobactin has demonstrated less than one to one coordination of ferric ions and the stoichiometry in aqueous solution also varies depending upon solution pH (Persmark and Neilands, *Biometals.* 1992 Spring;5(1):29-36). In an embodiment, a siderophore-transition metal cation A further characteristic of a siderophore transition metal cation complex is the presence of absence of one or more ligands present at coordination sites on the transition metal cation. As an example, a transition metal cation can have one or more sites that are occupied by labile aquo ligands, which are amenable to displacement by a moiety of the target molecule, such as the phosphate moiety of a phosphorylated molecule.

The choice of siderophore transition metal cation complex for use with a particular type of target molecule, such as a phosphorylated molecule, nitrotyrosine-containing molecule, sulfated molecule or a species within these broad categories of target molecules, generally can be determined empirically using procedures disclosed herein, as well as by using routine methods.

Methods described herein are carried out under conditions that allow a capture agent to bind a target molecule to form a target molecule-capture agent complex. A capture agent generally will bind to a target molecule under typical protein interaction assay conditions. Such conditions are well known to those skilled in the art and generally include roughly physiologically salt levels, a buffering agent, and a temperature in the range of 4-37 degrees C. For a chosen capture agent, a sample can be adjusted or placed into a solution or environment to have a specified characteristic such as a specified pH or salt concentration. The ability of a capture agent to bind selectively to a target molecule can be improved, enhanced and/or stabilized in the presence of sample ingredients such as inorganic salts, alcohols, detergents and surfactants, if desired. In an embodiment of a method of the invention, a capture agent is contacted with a sample in the absence of a salt, such as in the absence of an anionic component of a transition metal salt or in the absence of sodium chloride or other salt added for purposes of increasing buffer ionic strength. In another embodiment, a capture agent is contacted with a sample in the absence of acid, such as at a neutral pH of about 6 to 8, such as about pH 7. In certain embodiments of the present invention, a target molecule isolated and/or detected using a method of the invention is contained in a sample solution. In other embodiments of the present invention, the target molecule includes a support. If desired, one or more types of target molecules can be presented on a support while other types are presented in solution. Methods for attaching a target molecule to a support are described herein below.

Methods described herein can involve separating a target molecule-capture agent complex from a sample, thereby isolating the target molecule from the sample. Separation of the target molecule-capture agent complex can be achieved by a variety of well known means. In certain embodiments, a capture agent and/or a sample (i.e. a target molecule contained in the sample) can be attached to a support. When a portion of a target molecule-capture agent complex is attached to a support, a separation can be performed by removing a liquid phase from the support and/or by washing the support to remove a liquid phase, gel, colloidal, or other type of non-liquid phase from the support. Alternatively, separation can be performed by collecting the target molecule-capture agent complex, or a portion thereof, using a binding partner such as an antibody, ligand, receptor, antigen, complementary sequence, and the like, which selectively binds to an epitope within the target molecule-capture agent complex.

Methods descried herein can involve detecting formation of a target molecule-capture agent complex in order to detect the presence of the target molecule in a sample. Procedures for detecting interaction between molecular entities are well known to those skilled in the art. Such detection procedures generally involve detecting a physicochemical change in at least one of the interacting entities, or detecting the presence of one of the interaction entities when the presence of the other entity is known. A target molecule-capture agent complex or portion thereof can be detected by observing a physiochemical property as well as by observing a functional activity. A physicochemical property such as mass, fluorescence absorption, emission, energy transfer, polarization, anisotropy, and the like, can be observed without chemical modification of the target molecule-capture agent complex, if desired. Alternatively, the complex or a portion thereof can be subjected to some type of chemical modification that facilitates detection of a physicochemical property. A functional property such as interaction capability, enzymatic activity and the like can be observed by contacting the target molecule-capture agent complex or portion thereof, with an appropriate binding partner, for example an antibody, antigen, receptor, ligand, co-factor, subunit, complementary sequence, substrate and the like.

Exemplary well known methods for detecting molecular complexes and components thereof include measurements of absorbance, transmission, mass, charge to mass ratio, fluorescence intensity, fluorescence polarization, time-resolved fluorescence, resonance light scattering, surface-enhanced Raman scattering, electron paramagnetic resonance, refractive index absorbance, nuclear magnetic resonance, microcalorimetry, surface plasmon resonance, refractive index changes, spectropolarimetry, ellipsometry and a variety of spectroscopic characteristics such as those measurable by inductively-coupled plasma mass spectrometry, Fourier transform infrared spectrometry, and atomic absorption spectrometry.

When a capture agent or target molecule contained in (or subsequently separated from) a target molecule-capture agent complex contains a luminescent or dye component, detection can be by visual observation on a UV transilluminator, or by using a UV-based CCD camera detection system, a laser-based gel scanner, a xenon-arc-based CCD camera detection system, a Polaroid camera combined with a UV-transilluminator as well as a variety of other devices used for detecting luminescence.

As a non-limiting example of detecting a capture agent attached to a target molecule-capture agent complex, resonance light scattering (RLS) particles can be used as detectable tags (see for example, Yguerabide and Yguerabide, 2001 *J Cell Biochem Suppl.* Suppl 37:71-81). For example, spherical gold and silver RLS nanoparticles of uniform dimension ranging, for example, between approximately 40 and 120 nm diameter generate monochromatic scattered light when illuminated with a narrow beam of white light. The scattered light signal generated by a single RLS nanoparticle is roughly $10^4$ to $10^6$ times greater than the signal obtained for a conventional small molecule fluorophore and relatively easily detected by dark field illumination. The intensity and color of the scattered light generated by individual RLS particles is photostable and dependent upon the particle's composition and diameter. The surface of RLS particles can be derivatized with a variety of functionalities to induce specific binding in analytical assays. Sensitive RLS reagent and instrumentation systems for microarrays, immunocytology/histology, in situ hybridization, microtiter well assays and polypeptides or peptides on microarrays by the RLS technique, gold or silver nanoparticles are coated with siderophores and then charged with an appropriate transition metal cation. The particles are incubated on the microarray surface and excess particles are washed away. Bound particles are detected by resonance light scattering and phosphorylated targets are thus identified based upon the coordinates of the signal on the array.

Detection procedures including mass spectrometry methods can be used to detect target molecule-capture agent complexes. For example on-line capillary liquid chromatography-electrospray mass spectrometry and tandem mass spectrometry have been used to identify and characterize the siderophores of the fire blight pathogen *Erwinia amylovora*, including proferrioxamines D2, E, G1, G2, X1, and X2 (Gottfried et al. (2005) *Organic Mass Spectrometry* 28(3): 163-175.) Those skilled in the art will be able to perform similar procedures to detect a siderophore present in or released from a target molecule-capture agent complex.

Various types of proximity assays can be used to detect a target molecule-capture agent complex. Such proximity assays include, for example, scintillation proximity assays, AlphaScreen™ assays, etag™ assays (Aclara Biosciences, Mountain View, Calif.) and the like. Those skilled in the art of assay design will readily be able to use a proximity assay to detect formation of a target molecule-capture agent complex.

The invention provides a method involving contacting a sample with: a capture agent comprising a siderophore and transition metal cation, (ii) a target molecule binding partner linked to a photosensitizer capable of activating oxygen to singlet state, and (iii) a chemiluminescent compound capable of reacting with singlet oxygen, under conditions wherein the agent is capable of binding a target molecule to form a target molecule-capture agent complex; applying light to the sample, whereby the photosensitizer becomes excited; and detecting luminescence from the sample, wherein the luminescence indicates the presence or absence of the target molecule in the sample. In an embodiment, the target molecule binding partner is an antibody. The capture agent binds to the target molecule, while the capture agent binding partner binds to a different portion of the target molecule.

Further examples of procedures for detecting a target molecule-capture agent complex are described herein below. Example 1 describes fluorescence detection of target molecules. Example 2 describes fluorescence resonance energy transfer detection of target molecules. Example 3 describes elemental analysis detection of target molecules by virtue of detecting transition metal ions associated with the siderophore contained in the capture agent. Although this example focuses on ICP-MS, it is understood that a variety of elemental analysis approaches can be used for detecting a transition metal ion contained in a capture agent or a portion of the capture agent.

Previous work has shown that phosphoproteins can be selectively detected in gels through alkaline hydrolysis of phosphate esters of serine or threonine, precipitation of the released inorganic phosphate with calcium, formation of an insoluble phosphomolybdate complex and then visualization of the complex with a dye such as methyl green, malachite green or rhodamine B (Cutting and Roth, 1973 *Anal Biochem.* 1973 Aug;54(2):386-94; Debruyne, 1983 *Anal Biochem.* Aug;133(1):110-5). This staining procedure is fairly complex (involving seven different reagents) and alkaline hydrolysis requires heating gels to 65 degrees centigrade, which causes the gel matrix to hydrolyze and swell considerably. As phosphotyrosine residues are not hydrolyzed by the alkaline treatment, proteins phosphorylated at this amino acid residue escape detection by the method. The method described in Example 4 and variations thereof can be used to detect a phosphorylated molecule having a phosphorylated tyrosine residue Example 4 describes use of a capture agent of the invention for detecting target molecules within a polyacrylamide matrix. This example describes preparing a capture agent by attaching a siderophore to a support and then introducing a transition metal cation. It is understood that that a siderophore coordinated with a transition metal cation also can be attached to a support. Moreover, it is understood that similar procedures, as can be readily determined by those skilled in the art, can be used for detecting a target molecule with a variety of matrices, such as agarose and other types of gels, membranes, papers, plastic particles, fibers and the like.

The invention provides commercial packages useful for carrying out a method in accordance with the technologies described herein. A commercial package of the invention contains a capture agent comprising a siderophore and a transition metal cation, or reagents useful for forming such a capture agent. Examples of reagent useful for forming a capture agent include a siderophore lacking substantial metal cation coordination, together with one or more transition metal cation sources, such as a solution containing ransition metal salt, or a transition metal salt. A commercial package can include two or more siderophores and/or two or more transition metal cation sources, if desired.

A commercial package of the invention can contain a variety of components in addition to a capture agent; siderophore and transition metal cation; or siderophore and transition metal salt. A package can contain, for example, a set of instructions for preparing a capture agent, for using a capture agent to isolate a target molecule; for using a capture agent to detect a target molecule, or a combination of instructions. Instructions optionally can include a recommendation regarding the concentration of siderophore or the ratio of siderophore or capture agent to sample for use in a particular application, as well as guidance regarding temperature, buffer conditions and incubation time periods. A commercial package of the invention optionally can contain other components, such as one or more protein or peptide fractionation devices, labeled polypeptides, fluorescent dyes, binding buffers, wash buffers, molecular weight standards, isoelectric point standards, phosphorylation standards, fixatives, stains, antibodies, lectins, aptamers, phosphatase substrates, kinase substrates and the like. Those skilled in the art will be able to select suitable components for inclusion in a commercial package of the invention based on such exemplary factors as design of the assay protocol, the specific capture agent used for detection or isolation, method of measurement to be employed once the assay has been performed, consumer price point, shipping and handling suitability and the like.

The invention provides various commercial packages. One commercial package contains an isolated siderophore and a transition metal salt. Another commercial package contains an isolated siderophore and a transition metal solution. A variety of isolated siderophores and transition metal salts or solutions can be contained in a commercial package of the invention. In an embodiment, the siderophore is attached to a support.

The invention provides compositions useful for carrying out a method described herein. A composition of the invention can include, for example, a siderophore coordinated with one or more transition metal cations, such as a desferrioxamine complexed with gallium (III). Such a siderophore-transition metal cation complex can be attached to a support, can contain a ligand in addition to a siderophore, and can include a tag if desired.

The invention provides methods for identifying a capture agent suitable for use in detecting or isolating a target molecule as described herein. The method involves contacting a siderophore-transition metal cation-complex with a phosphorylated moiety, and determining the ability of the complex to bind to the phosphorylated moiety, thereby identifying a capture agent. The method can further involve contacting a siderophore with a transition metal cation, and determining the ability of the siderophore to bind to the transition metal cation, wherein a siderophore that binds to the transition metal cation is identified as a siderophore-transition metal cation-complex.

In an embodiment, the siderophore is contacted with a transition metal cation in the presence of a detectable transition metal cation-binding substance, and the ability of the siderophore to displace the detectable transition metal cation-binding substance to form a siderophore-transitional metal cation complex is determined. The siderophore-transition metal cation-complex can be contacted, for example, with a detectable phosphorylated moiety. In another embodiment, the ability of the complex to bind to the phosphorylated moiety is determined by detecting hydrolysis of the detectable moiety. In a specific embodiment, the detectable phosphorylated moiety is selected from the group of 6, 8-difluoro-4-methylumbelliferyl and 4-nitrophenyl phospho.

When fluorescent siderophores complex with ferric iron ions, the fluorescence intensity or quantum yield of the luminescent species is decreased (Palanche et al, *J Biol Inorg Chem.* 1999 Apr;4(2):188-98). For example, the fluorescence of unchelated pyroverdins arises from the quinoline chromophore, which is bound to a peptide chain and to a dicarboxylic acid or a dicarboxylic amide, but the Fe(III)-chelated pyroverdins do not fluoresce. Quenching is thought to occur through the formation of a ground state complex between the fluorophore and the ferric metal ion. Without wishing to be bound by theory, it appears that the paramagnetic properties of ferric iron cations tend to promote dissipation of the excited state energy in a nonradiative process by an enhancement of the intersystem crossing process. Paramagnetism in the transition elements is caused by the presence of unpaired electrons in the d sub-orbital. Diamagnetism, on the other hand, is characteristic of compounds where all the electrons are paired in the d orbitals. The diamagnetic gallium (III) ion can often serve as a functional analogue of the ferric iron atom in iron-containing biomolecules, and complexes of this type retain their fluoresecent properties.

An exemplary procedure for determining the ability of a siderophore-transition metal cation complex to bind to-a phosphorylated molecule involves monitoring hydrolysis of a fluorogenic or chromogenic phosphate monoester-or phosphate diester-containing substrate, such as 6,8-difluoro-4-methylumbelliferyl phosphate (DiFMUP) or 4-nitrophenyl phosphate (4-NPP) (Zhan and Sitrin, 2001). When a metal cation binds tightly to such a phosphorylated substrate through ligand exchange, the phosphoryl group is brought into close proximity with potential nucleophiles, such as hydroxide ions are activated water molecules, leading to the metal ion-catalyzed cleavage of the phosphate-oxygen bond and generation of a detectable signal. Such a substrate can be readily cleaved because of the relatively low pKa value of the fluorophore and chromophore leaving groups. A variety of other procedures can provide this type of information, and can use different substrates or instrumentation, such as nuclear magnetic resonance spectroscopy- and mass spectrometry-based approaches (Moss and Ragunathan, 1998 *Chem. Commun.* 1998 1871-1872).

It is understood that modifications that do not substantially affect the activity of the various embodiments of this invention are also included within the definition of the invention provided herein. Accordingly, the following examples are intended to illustrate but not limit the present invention.

EXAMPLE 1

Profiling of Phosphorylated Molecules Using Capture Agents

This example describes a procedure for profiling phosphorylated molecules using a capture agent in a microarray format.

To identify phosphorylated molecules contained in samples distributed on microarrays, a capture agent selective for phosphorylated molecules is used. The capture agent used in this example has a detectable fluorescence.

The assay is carried out as follows. Binding partners for phosphorylated molecules are immobilized as spots on the surface of a microarray. The binding partners can be, for example, antibodies, peptides, aptamers, and the like. The spots can contain different binding partners or can be replicate spots. A sample suspected to contain phosphorylated molecules capable of binding to the binding partners is applied to the microarray surface, and the microarray is incubated. As with conventional microarrays, incubation can be performed in the open, under a coverslip, or in an incubation instrument. After incubation, the sample is washed from the microarray to remove excess and non-selectively bound capture agents and other molecules. Buffers containing inorganic phosphate, such as phosphate-buffered saline, are generally avoided because phosphate can compete for binding of siderophores, and reduce the amount of siderophore bound to phosphorylated target molecules.

The resultant spots contain the binding partners plus whatever phosphorylated molecules have been selectively bound to them during incubation with the sample. A solution containing naturally fluorescent capture agent is then applied to the microarray and allowed selectively to the phosphorylated moieties of molecules present in spots of the microarray.

Fluorescence detection of the capture molecules is performed using methods and instrument types typically used for detection of conventional fluorescently labeled microarrays. As an example, a beam of excitation light having wavelengths overlapping the extinction band of the fluorescent moiety is directed to a beam-splitter element, which directs the excitation beam into the objective lens. The lens focuses the beam onto a small area of the microarray surface. If fluorescent siderophores are present at the focus, they emit fluorescence light at a longer wavelength. A fraction of the emitted fluorescence light is captured by the lens and formed into a beam. The beam-splitter passes a portion of the fluorescence light to a detector, such as a photomultiplier tube or CCD array. Typically an emission filter is placed before the detector to block any wavelengths not generated by siderophore fluorescence. The fluorescence signal is proportional to the local area concentration of the siderophore, and hence to the local concentration of phosphorylated residues. In some cases, replacement of the aqueous media bathing the microarray after the washing step with an organic solvent, such as n-octanol, or a solution containing an organic solvent, can increase the fluorescence intensity of the signal by about 10-fold or more.

In summary, a fluorescent capture agent can be used for detecting phosphorylated molecules in a microarray format.

EXAMPLE 2

Enzyme Assays Using Capture Agents

This example describes procedures for measuring enzyme activity using capture agents.

Capture agents can be used in assays for detecting enzyme activity, such as the activity of protein kinases, phosphatases and phosphodiesterases. As an example, a peptide substrate, when phosphorylated by a protein kinase, can bind to a fluorescent capture agent through its phosphorylated moiety. This binding of phosphorylated peptide substrate to the capture agent can decrease mobility of the substrate and result in an increased fluorescence polarization signal. Alternatively a fluorescently-labeled peptide substrate can be used with a nonfluorescent capture agent to obtain similar results.

In another type of assay, a fluorescent capture agent and a fluorophore-labeled peptide substrate for a particular kinase are added to a sample suspected to contain the kinase. Peptide that is phosphorylated by the kinase can bind to the capture agent. The capture agent contains a fluorescent siderophore, such as azobactin, which is an exemplary naturally fluorescent siderophore that typically absorbs at about 365 nm and emits at about 480 nm. However, if the peptide itself is labeled with Texas Red dye, excitation of the siderophore at 365 nm leads to an emission shift to the longer wavelength of 613 nm through the process of fluorescence resonance energy transfer (FRET). By detecting the emission shift, the presence of phosphorylated peptide bound to capture agent can be detected. By analogy, homogenous time-resolved fluorescence-based assays can also be created whereby, for example, a europium based chelate is affixed to the kinase substrate peptide and capture agent is attached to a fluorescent protein, such as allophycocyanin. The europium chelate absorbs at 350 nm and if the capture agent-labeled fluorescent protein is in close proximity to the peptide, through interaction of the phosphorylated moiety on the peptide with the transition metal cation on the siderophore, the emission wavelength shifts from about 620 nm to 665 nm. The energy transfer occurs between the two fluorescent moieties in each of the cited examples due to overlap between the emission of the donor dye and absorption of the acceptor dye. The labeled siderophore can serve as either the donor or the acceptor in FRET assays. Phosphatase assays can be performed using the same basic principles as described for kinase assays, by monitoring loss of signal at the longer emission wavelength, which would indicate loss of target peptide interaction with capture agent, as the peptide progressively becomes dephosphorylated.

In summary, formation or destruction of a phosphorylated molecule can be detected using a capture agent. Detection can employ a variety of fluorescence methods, such as fluorescence resonance energy transfer, fluorescence polarization and the like. It is understood that this general methodology is applicable to other types of target molecules, such as nitrotyrosine-containing molecules and sulfated molecules.

EXAMPLE 3

Detection of Target Molecules Using Capture Agents with Elemental Analysis Approaches This example describes detecting target molecules that bind to capture agents by virtue of detecting transition metal ions associated with their siderophores.

This example describes one type of analytical approach for elemental analysis—inductively-coupled plasma mass spectrometry (ICP-MS). Using ICP-MS, as little as 1 part per billion (ppb) of metal ions can be detected. The ionized conversion of aluminum, which has a first ionization potential of 5.986 electron volts, is 99% under identical run conditions as described for phosphorous in Wilbur and McCurdy, 2001. Thus, following the procedure outlined in Wilbur and McCurdy, 2001 for detecting Al (III) instead of phosphorous improves detection 16-fold. In addition, the specific detection of the metals can move the detection window away from sample background signal.

For the sake of background, inductively-coupled plasma mass spectrometry (ICP-MS) is useful for trace elemental analysis of environmental, biological, and pharmaceutical samples. Laser ablation ICP-MS permits trace element analysis by combining the spatial resolution of an ultraviolet laser beam with the mass resolution and element sensitivity of a modern ICP-MS. UV laser light, usually produced at a wavelength of 193-266 nm is focused on a sample surface, causing sample ablation. Ablation craters of 15-20 microns are routinely produced by the instrumentation. No special sample preparation is required for the procedure. Ablated material is transported in an argon carrier gas directly to the high temperature inductively-coupled plasma and the resulting ions are then drawn into a mass spectrometer for detection and counting. A mass filter selects particles on the basis of their charge/mass ratio so that only specific isotopes are allowed through the filter and can enter the electron multiplier detector mounted at the end of the mass spectrometer (quadrupole, magnetic sector or time-of-flight instrumentation). Detected signals of individual isotopes can be converted to isotopic ratios or, when standards are measured along with the unknowns, to the actual element concentrations.

ICP-MS-based detection of target molecule-capture agent complexes can be performed according to the following exemplary procedure. First, target molecules are bound to spots of immobilized binding partners (for example, antibodies, aptamers, or any other affinity molecule selective for the target(s)) contained on a microarray. Then, the array is incubated with one or more capture agents. Next, the array is washed in a buffer, such as 50 mM sodium acetate, pH 6.0, 50 mM magnesium chloride to remove excess capture agent. The individual spots on the array are subjected to laser ablation ICP-MS by methods similar to those described, for example, in Marshall et al, 2002 and Wind et al, 2003, except that the relevant metal signal is quantified (rather than the phosphorous signal.) Detection using a laser-ablation ICP-mass spectrometer instrument is generally carried out by directing an ultraviolet laser ablation beam, usually in the form of a collimated beam, toward a focusing lens. The lens can focus the beam to a high flux density on a particular microarray spot, causing local ablation. The ablated molecules are captured in an ICP sampling tube, where they are carried by a flow of carrier gas away from the microarray. The carrier gas is generally provided in a manner that floods the vicinity of the area subject to ablation. The carrier gas and ablated molecules are carried to an ICP-mass spectrometer instrument where the molecules are ionized in the plasma followed by mass identification in the spectrometer. Sampling can be performed by single or multi-spot analysis, straight line scans or rastering.

In summary, a target molecule in a sample can be detected by performing elemental analysis on target molecule-capture agent complexes or the siderophore-transition metal cation portion thereof.

EXAMPLE 4

Detection of Target Molecules Present in a Matrix

This example describes use of a capture agent of the invention for detecting target molecules within a polyacrylamide matrix.

To detect target polypeptides in a polyacrylamide matrix, a polypeptide sample is separated by SDS-polyacrylamide gel electrophoresis according to standard procedures. After electrophoresis, the gel incubated in a fixative solution containing an acid and an alcohol, such as 50% methanol, 10% acetic acid. The gel is then washed in deionized water to remove fixative solution. Next the gel is incubated in a solution containing a fluorescent capture agent for at least about two hours with gentle shaking (for example, ~50 RPM on an orbital shaker). The solution containing fluorescent capture agent can contain simple alcohols, buffer, salts, acids and combinations thereof, in order to facilitate interaction with target polypeptides and reduce non-selective binding to the gel matrix or other anionic macromolecules within the sample. The gel is then washed in deionized water or buffer. The target polypeptides, such as phosphoproteins, can then detected using a variety of methods suitable for observing a fluorescent signal. Similar approaches are employed when detecting electrobloted target polypeptides on polymeric membranes, such as nitrocellulose or polyvinylidene difluoride membranes. Generally, incubation periods are shorter for transfer membranes due to better accessibility of polypeptides to the detection reagents.

In summary, a capture agent can be used for target molecule detection in a matrix such as a polyacrylamide gel.

EXAMPLE 5

Preparation of a Capture Agent Attached to a Support

This example describes preparation of desferrioxamine capture agents attached to a plastic bead support.

To prepare desferrioxamine complexed with gallium (III) cation and desferrioxamine complexed with iron (III), as a capture agents attached to a plastic bead support, desferrioxamine was first attached to plastic beads as follows: 5 mg of deferoxamine, 250 ul of raw AlphaScreen™ acceptor beads (at 20 mg/ml), 6 ul of TWEEN™ 20 detergent (at 10% in water), 50 ul of sodium cyanoborohydride (at 25 mg/ml in water) and 695 ul of MES 0.1 M, pH 6.0 were mixed. The mixture was incubated overnight at 37° C. in an agitating water bath. The following morning, 50 ul of carboxymethoxylamine (at 65 mg/ml in water, pH 5) was added, and the mixture was incubated for 1 hour at 37° C. The beads were then centrifuged (30 minutes at 13,000 rpm), washed twice with TRIS buffer (0.1 M, pH 8.0).

To form a complex of desferrioxamine with transition metal cations, the beads were resuspended in HEPES buffer (25 mM, pH 7.4) containing 100 mM gallium (III) or iron (III) chloride. After 1 hour of incubation, the beads were centrifuged, washed twice with HEPES buffer (25 mM pH 7.4) and resuspended in HEPES buffer. Sonication optionally can be used to eliminate aggregates of beads. Raw AlphaScreen acceptor beads were obtained from PerkinElmer® (Boston, Mass.). Desferrioxamine, sodium cyanoborohydride, carboxymethoxylamine, gallium (III) chloride, sodium chloride and TWEEN™ 20 were obtained form Sigma-Aldrich (St. Louis, Mo.). MES, TRIS and HEPES buffer salts were obtained from ICN (MP Biomedicals, Irvine, Calif.).

EXAMPLE 6

Isolation and Detection of Target Molecules using Desferrioxamine Capture Agents This example describes isolating and detecting phosphopeptides, phospholipids, nitrotyrosine-containing peptides and sulfated polypeptides using deferoxamine-gallium (III) cation capture agents.

The ability of deferoxamine-gallium (III) cation capture agents to bind to target molecules was confirmed using AlphaScreen™ assays. These assays are bead-based non-radioactive, homogeneous proximity assays. For a description of AlphaScreen™ assay methods, see for example Ullman E F, et al. *Proc. Natl. Acad. Sci USA*, 91:5426-5430 (1994), U.S. Pat. Nos. 6,251,581; 6,180,354, and ALPHASCREEN Practical Guide, PerkinElmer, Inc. (2003), each of which are incorporated herein by reference. Briefly, the assay employs two types of beads, donor beads and acceptor beads. Each bead type contains a different mixture of chemicals. Donor beads contain a photosensitizer, which converts ambient oxygen to an excited from of O2, singlet oxygen upon illumination at 680 nm. Within its 4 microsecond half-life, singlet oxygen can diffuse approximately 200 nm in solution. If an Acceptor bead is within that proximity, energy is transferred from the singlet oxygen to thioxene derivatives with the Acceptor bead, subsequently culminating in light production at 520-620 nm. In the absence of an Acceptor bead, singlet oxygen falls to ground state and no signal is produced. Proximity of Acceptor to Donor beads depends on the interaction of the molecules bound to them. The most common AlphaScreen assay is constructed by capturing one binding partner, such as a target molecule, onto the Donor beads and the other partner, such as a target molecule binding partner, onto the Acceptor beads, When the partners interact, chemical energy is transferred from Donor to Acceptor beads and a signal is produced. Alternatively, competition or cleavage assays can be read as signal reduction. Donor and Acceptor beads are commercially available from PerkinElmer LAS, Inc. (Boston, Mass.) as conjugates, such as conjugates with antibodies such as anti-phosphomolecule antibodies, and in unconjugated form. Unconjugated beads can be coated directly to a binding partner via a simple reductive amination protocol.

AlphaScreen™ assays were performed using a various biotinylated target molecules as follows: In a white 384-well plate were added in order: 5 ul of biotinylated target molecule, referred to as "probe" in FIG. 5 (from 10 uM to 10 pM) diluted in HEPES 25 mM, 100 mM NaCl 0.01% Tween 20 and 10 ul of deferoxamine-gallium (III) cation acceptor beads at 50 ug/ml in HEPES buffer. After 30 minutes incubation at RT, 10 ul of streptavidin donor beads (50 ug/ml in HEPES buffer), which bind selectively to the biotinylated target molecules, was added and the plate was incubated for 1 hour at room temperature. Finally, the plate was read on an AlphaQuest™ reader. All assays were done in triplicate. Biotinylated phosphotyrosine target molecules and streptavidin AlphaScreen™ donor beads were obtained from PerkinElmer® (Boston, Mass.)

Figure 2:
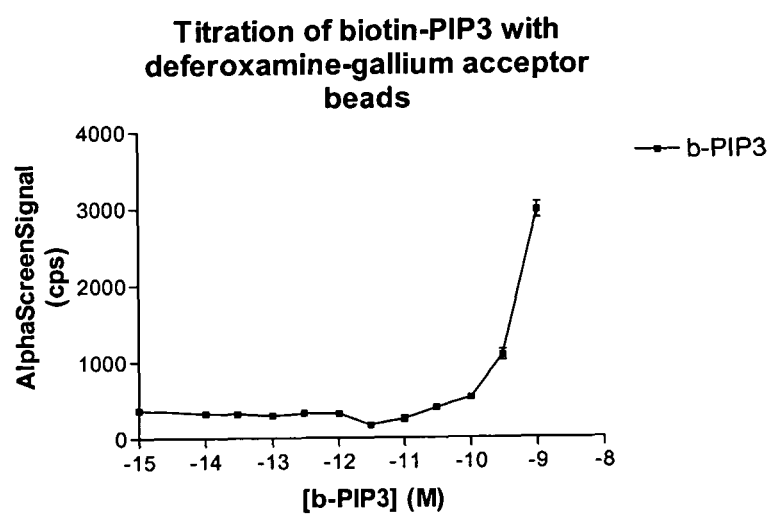
FIG. 2 shows detection of phosphoinositide using a capture agent that includes a siderophore coordinated with a transition metal cation.
Figure 3:
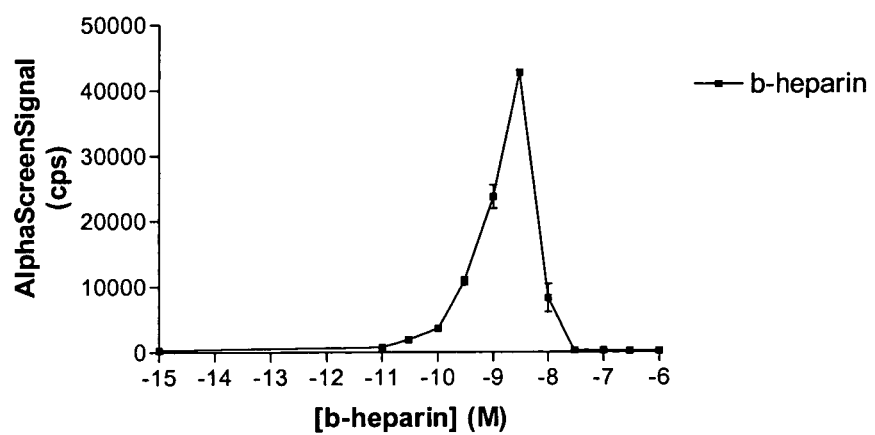
FIG. 3 shows detection of a sulfated molecule using a capture agent that includes a siderophore coordinated with a transition metal cation.
Figure 4:
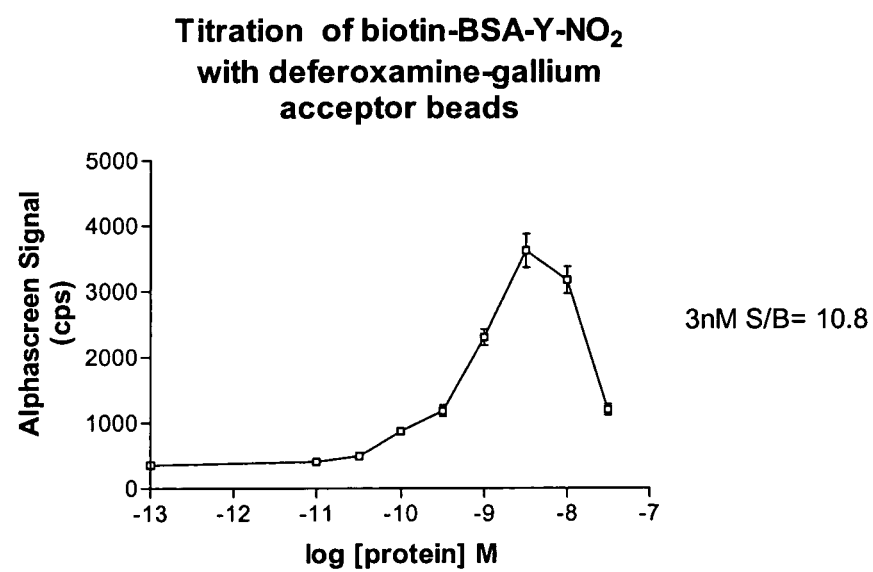
FIG. 4 shows detection of a nitrotyrosine-containing molecule using a capture agent that includes a siderophore coordinated with a transition metal cation.
Figure 5:
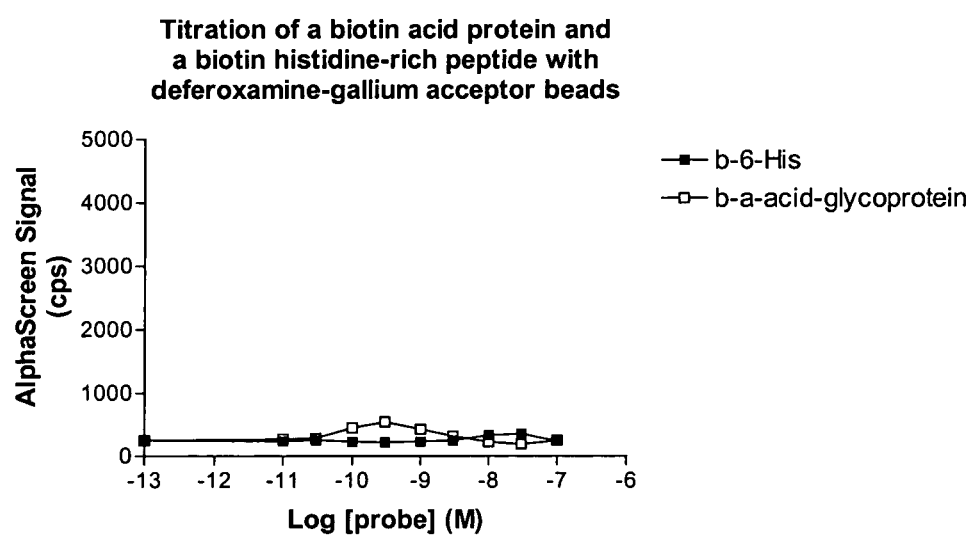
FIG. 5 shows inability of biotin acidic proteins and histidine-rich peptides to bind to a capture agent that includes a siderophore coordinated with a transition metal cation.

As is shown in FIG. 1, isolated biotin-phospho-Ick was detected, starting at around 300 pM phosphopeptide concentration with a signal-to-background of 9.7. Maximum signal-to-background was found to be around 800 at 30 nM phosphopeptide. As is shown in FIG. 2, biotin-phosphoinositide- 3,4,5-trisphosphate (PIP3) was detected, starting at around 300 pM biotin-PIP3. Maximal signal was not yet reached at 1M. As is shown in FIG. 3, biotin-heparin was detected, starting at around 30 pM biotin-heparin. Signal was maximal at about 3 nM with a signal to noise ratio of 145. As is shown in FIG. 4, biotin-nitrotyrosine-BSA was detected, starting at around 100 pM biotin-nitrotyrosine-BSA. Signal was maximal at 3 nM with a signal to noise ratio of 10.8. As is shown in FIG. 5, neither acidic polypeptides nor histidine-rich peptides bound to the deferoxamine-gallium complex.

In summary, this example shows use of deferoxamine-gallium (III) cation capture agents in detecting phosphopeptides, phospholipids, nitrotyrosine-containing peptides and sulfated polypeptides.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method for determining the presence of a target molecule in a biological sample at physiological pH, comprising:
    (a) contacting a biological sample with a capture agent at physiological pH, the capture agent comprising a hydroxamate siderophore complexed with a transition metal cation as a binding moiety, under conditions wherein the binding moiety of the capture agent is capable of selectively binding a target molecule to form a target molecule-capture agent complex, wherein the target molecule is selected from the group consisting of a phosphorylated molecule, a nitrotyrosine-containing molecule and a sulfated molecule, and
    (b) detecting formation of the target molecule-capture agent complex in the biological sample at physiological pH, thereby determining the presence of the target molecule in the biological sample;
    wherein the biological sample is not washed or purified prior to detecting formation of the target molecule-capture agent complex in the biological sample.

2. The method of claim 1, wherein the detecting is performed by measuring binding between the capture agent and the target molecule.

3. The method of claim 2, wherein the measuring comprises a mode selected from the group of absorbance, transmission, mass measurement, fluorescence intensity, fluorescence polarization, time-resolved fluorescence, resonance light scattering, surface-enhanced Raman scattering, inductively-coupled plasma mass spectrometry, electron paramagnetic resonance, refractive index absorbance, nuclear magnetic resonance, microcalorimetry, Fourier transform infrared spectrometry, atomic spectrometry, surface plasmon resonance, refractive index changes, spectropolarimetry and ellipsometry.

4. The method of claim 1, wherein the hydroxamate siderophore portion of the target molecule-capture agent complex is detected.

5. The method of claim 1, wherein the transition metal portion of the target molecule-capture agent complex is detected.

6. The method of claim 1, wherein the phosphorylated molecule portion of the target molecule-capture agent complex is detected.

7. The method of claim 1, wherein the target molecule is a phosphorylated molecule.

8. The method of claim 1, wherein the hydroxamate siderophore is desferrioxamine.

9. The method of claim 1, wherein the transition metal cation is iron (III).

10. The method of claim 1, wherein the hydroxamate siderophore is desferrioxamine, the transition metal cation is iron (III), and the target molecule is a phosphorylated molecule.

11. The method of claim 1, wherein the phosphorylated molecule comprises a polypeptide.

12. The method of claim 1, wherein the phosphorylated molecule comprises a peptide.

13. The method of claim 10, wherein the phosphorylated molecule comprises a polypeptide.

14. The method of claim 10, wherein the phosphorylated molecule comprises a peptide.

15. The method of claim 1, wherein the physiological pH is about 7.4.

16. The method of claim 1, wherein the biological sample is selected from the group consisting of biological fluids, whole organisms, organs, tissues, cells, culture medium, subcellular organelles, protein complexes, individual proteins, recombinant proteins, fusion proteins, viruses, viral particles, biopsy samples, peptides and amino acids.

* * * * *